US012078192B2

United States Patent
Gross-Hardt et al.

(10) Patent No.: US 12,078,192 B2
(45) Date of Patent: Sep. 3, 2024

(54) NON-OCCLUDING INTRA VASCULAR BLOOD PUMP PROVIDING REDUCED HEMOLYSIS

(71) Applicant: Procyrion, Inc., Houston, TX (US)

(72) Inventors: Sascha Gross-Hardt, Aachen (DE); Tim Kaufman, Aachen (DE); William L. Clifton, Houston, TX (US); Benjamin A. Hertzog, Houston, TX (US); Jason J. Heuring, Houston, TX (US)

(73) Assignee: Procyrion, Inc., Houston, TX (US)

( * ) Notice: Subject to any disclaimer, the term of this patent is extended or adjusted under 35 U.S.C. 154(b) by 0 days.

(21) Appl. No.: 17/588,991

(22) Filed: Jan. 31, 2022

(65) Prior Publication Data
US 2022/0226634 A1 Jul. 21, 2022

Related U.S. Application Data

(63) Continuation of application No. 15/276,590, filed on Sep. 26, 2016, now Pat. No. 11,235,138.
(Continued)

(51) Int. Cl.
*F04D 3/02* (2006.01)
*A61M 60/135* (2021.01)
(Continued)

(52) U.S. Cl.
CPC ............. *F04D 3/02* (2013.01); *A61M 60/135* (2021.01); *A61M 60/178* (2021.01);
(Continued)

(58) Field of Classification Search
CPC . F04D 3/02; F04D 3/005; F04D 3/024; F04D 29/181; A61M 60/205; A61M 60/237; A61M 60/806; A61M 60/856
See application file for complete search history.

(56) References Cited

U.S. PATENT DOCUMENTS 2,896,926 A 7/1959 Chapman
2,935,068 A 5/1960 Donaldson
(Continued)

FOREIGN PATENT DOCUMENTS

EP 2388029 11/2011
IT 31466 12/2010
(Continued)

OTHER PUBLICATIONS

Demirsoy, Ergun et al., Grafting the restenosed coronary artery after removal of multiple failed stents by endarterectomy, Texas Heart Institute Journal, Endarterectomy of Multiple Stents Before Grafts, 2006, vol. 33, No. 2, pp. 262-263.
(Continued)

*Primary Examiner* — Kenneth J Hansen
(74) *Attorney, Agent, or Firm* — Knobbe Martens Olson & Bear LLP

(57) ABSTRACT

A non-occluding intravascular pump comprises a shroud providing an inlet for incoming blood flow and an outlet for outgoing blood flow, wherein the shroud is a cylindrical housing; an impeller positioned within shroud, wherein a central axis of the shroud and impeller are shared; a motor coupled to the impeller, wherein the motor rotates the impeller to causes blood to be drawn through the inlet and output to the outlet, and the motor is centrally disposed and shares the central axis with the shroud and the impeller; and a plurality of pillars coupling the motor to the shroud, wherein the pillars secure the shroud in close proximity to the impeller. Various design features of the pump may be optimized to reduce hemolysis, such as, but not limited to, inlet length, impeller design, pillar angle, and outlet design.

17 Claims, 21 Drawing Sheets

Related U.S. Application Data

(60) Provisional application No. 62/233,025, filed on Sep. 25, 2015.

(51) Int. Cl.

| | |
|---|---|
| *A61M 60/178* | (2021.01) |
| *A61M 60/205* | (2021.01) |
| *A61M 60/237* | (2021.01) |
| *A61M 60/422* | (2021.01) |
| *A61M 60/806* | (2021.01) |
| *A61M 60/81* | (2021.01) |
| *A61M 60/857* | (2021.01) |
| *F04D 3/00* | (2006.01) |
| *F04D 13/02* | (2006.01) |
| *F04D 29/18* | (2006.01) |
| *F04D 29/52* | (2006.01) |
| *F04D 29/54* | (2006.01) |
| *A61F 2/06* | (2013.01) |

(52) U.S. Cl.
CPC ........ *A61M 60/205* (2021.01); *A61M 60/237* (2021.01); *A61M 60/422* (2021.01); *A61M 60/806* (2021.01); *A61M 60/81* (2021.01); *A61M 60/857* (2021.01); *F04D 3/005* (2013.01); *F04D 13/02* (2013.01); *F04D 13/021* (2013.01); *F04D 29/181* (2013.01); *F04D 29/528* (2013.01); *F04D 29/548* (2013.01); *A61F 2002/068* (2013.01); *F05D 2240/303* (2013.01); *F05D 2250/52* (2013.01)

(56) References Cited

U.S. PATENT DOCUMENTS

| | | | |
|---|---|---|---|
| 3,510,229 A | 7/1968 | Smith | |
| 3,455,540 A | 7/1969 | Marcmann | |
| 3,620,584 A | 11/1971 | Rosenweig | |
| 3,812,812 A | 5/1974 | Hurwitz | |
| 4,127,384 A | 11/1978 | Fahlvik et al. | |
| 4,141,603 A | 2/1979 | Remmers et al. | |
| 4,304,524 A | 12/1981 | Coxon | |
| 4,407,508 A | 10/1983 | Raj et al. | |
| 4,613,329 A | 9/1986 | Bodicky | |
| 4,625,712 A | 12/1986 | Wampler | |
| 4,643,641 A | 2/1987 | Clausen et al. | |
| 4,753,221 A | 6/1988 | Kensey et al. | |
| 4,846,152 A * | 7/1989 | Wampler ............ A61M 60/237 | |
| | | | 600/16 |
| 4,900,227 A | 2/1990 | Trouplin | |
| 4,919,647 A | 4/1990 | Nash | |
| 4,944,722 A | 7/1990 | Carriker et al. | |
| 4,969,865 A | 11/1990 | Hwang et al. | |
| 4,994,017 A | 2/1991 | Yozu | |
| 5,007,513 A | 4/1991 | Carlson | |
| 5,147,388 A | 9/1992 | Yamazaki | |
| 5,201,679 A | 4/1993 | Velte, Jr. et al. | |
| 5,207,695 A | 5/1993 | Trout, III | |
| 5,211,546 A | 5/1993 | Isaacson et al. | |
| 5,368,438 A | 11/1994 | Raible | |
| 5,393,197 A | 2/1995 | Lemont et al. | |
| 5,405,383 A | 4/1995 | Barr | |
| 5,490,763 A | 2/1996 | Abrams et al. | |
| 5,527,159 A | 6/1996 | Bozeman, Jr. et al. | |
| 5,534,287 A | 7/1996 | Lukic | |
| 5,588,812 A | 12/1996 | Taylor et al. | |
| 5,613,935 A | 3/1997 | Jarvik | |
| 5,660,397 A | 8/1997 | Holtkamp | |
| 5,686,045 A | 11/1997 | Carter | |
| 5,722,930 A | 3/1998 | Larson, Jr. et al. | |
| 5,725,570 A | 3/1998 | Heath | |
| 5,749,855 A | 5/1998 | Reitan | |
| 5,824,070 A | 10/1998 | Jarvik | |
| 5,827,171 A | 10/1998 | Dobak, III et al. | |
| 5,911,685 A | 6/1999 | Siess et al. | |
| 5,921,913 A | 7/1999 | Seiss | |
| 5,947,703 A | 9/1999 | Nojiri et al. | |
| 5,951,263 A | 9/1999 | Taylor et al. | |
| 5,964,694 A | 10/1999 | Siess et al. | |
| 6,007,478 A | 12/1999 | Siess et al. | |
| 6,136,025 A | 10/2000 | Barbut et al. | |
| 6,227,797 B1 | 5/2001 | Watterson et al. | |
| 6,245,026 B1 | 6/2001 | Campbell et al. | |
| 6,253,769 B1 | 7/2001 | LaFontaine et al. | |
| 6,302,910 B1 | 10/2001 | Yamazaki et al. | |
| 6,517,315 B2 | 2/2003 | Belady | |
| 6,527,699 B1 | 3/2003 | Goldowsky | |
| 6,533,716 B1 | 3/2003 | Schmitz-Rode et al. | |
| 6,547,519 B2 | 4/2003 | deBlanc et al. | |
| 6,585,756 B1 | 7/2003 | Strecker | |
| 6,609,883 B2 | 8/2003 | Woodard et al. | |
| 6,616,323 B2 | 9/2003 | McGill | |
| 6,638,011 B2 | 10/2003 | Woodard et al. | |
| 6,645,241 B1 | 11/2003 | Strecker | |
| 6,660,014 B2 | 12/2003 | Demarais et al. | |
| 6,716,189 B1 | 4/2004 | Jarvik et al. | |
| 6,733,459 B1 | 5/2004 | Atsumi | |
| 6,749,598 B1 | 6/2004 | Keren et al. | |
| 6,860,713 B2 | 3/2005 | Hoover | |
| 6,866,805 B2 | 3/2005 | Hong et al. | |
| 6,887,215 B2 | 5/2005 | McWeeney | |
| 6,972,956 B2 | 12/2005 | Franz et al. | |
| 7,011,620 B1 | 3/2006 | Siess | |
| 7,125,376 B2 | 10/2006 | Viole et al. | |
| 7,189,260 B2 | 3/2007 | Harvath et al. | |
| 7,374,531 B1 | 5/2008 | Kantrowitz | |
| 7,381,034 B2 | 6/2008 | Shishido | |
| 7,393,181 B2 | 7/2008 | McBride et al. | |
| 7,396,327 B2 | 7/2008 | Morello | |
| 7,473,220 B2 | 1/2009 | Francese et al. | |
| 7,534,258 B2 | 5/2009 | Gomez et al. | |
| 7,682,673 B2 | 3/2010 | Houston et al. | |
| 7,758,806 B2 | 7/2010 | Zhao | |
| 7,762,941 B2 | 7/2010 | Jarvik | |
| 7,841,976 B2 | 11/2010 | McBride et al. | |
| 7,878,967 B1 | 2/2011 | Khanal | |
| 7,914,436 B1 | 3/2011 | Kung | |
| 7,993,259 B2 | 8/2011 | Kang et al. | |
| 7,998,054 B2 | 8/2011 | Bolling | |
| 8,012,079 B2 | 9/2011 | Delgado, III | |
| 8,088,059 B2 | 1/2012 | Jarvik | |
| 8,123,669 B2 * | 2/2012 | Siess .................. A61M 60/178 | |
| | | | 600/16 |
| 8,177,703 B2 | 5/2012 | Smith et al. | |
| 8,403,824 B2 | 3/2013 | Foster | |
| 8,579,858 B2 | 11/2013 | Reitan et al. | |
| 8,591,393 B2 | 11/2013 | Walters et al. | |
| 8,597,170 B2 | 12/2013 | Walters et al. | |
| 8,641,594 B2 | 2/2014 | LaRose et al. | |
| 8,727,959 B2 | 5/2014 | Reitan et al. | |
| 8,731,664 B2 | 5/2014 | Foster et al. | |
| 8,734,508 B2 | 5/2014 | Hastings et al. | |
| 8,777,832 B1 | 7/2014 | Wang et al. | |
| 8,992,407 B2 | 3/2015 | Smith et al. | |
| 9,138,517 B2 | 9/2015 | Garrigue | |
| 9,138,518 B2 | 9/2015 | Campbell et al. | |
| 9,144,638 B2 | 9/2015 | Zimmermann et al. | |
| 9,162,018 B2 | 10/2015 | Foster | |
| 9,199,020 B2 | 12/2015 | Siess | |
| 9,265,870 B2 | 2/2016 | Reichenbach et al. | |
| 9,364,593 B2 | 6/2016 | McBride et al. | |
| 9,415,147 B2 | 8/2016 | Akkerman et al. | |
| 9,433,713 B2 | 9/2016 | Corbett et al. | |
| 9,486,566 B2 | 11/2016 | Siess | |
| 9,533,084 B2 | 1/2017 | Siess et al. | |
| 9,572,915 B2 | 2/2017 | Heuring et al. | |
| 9,616,159 B2 | 4/2017 | Anderson et al. | |
| 9,744,281 B2 | 8/2017 | Siegenthaler | |
| 9,759,222 B2 | 9/2017 | Zimmermann et al. | |
| 9,777,732 B2 | 10/2017 | LaRose et al. | |
| 9,907,890 B2 | 3/2018 | Muller | |
| 9,919,089 B2 | 3/2018 | Garrigue | |
| 10,039,873 B2 | 8/2018 | Siegenthaler | |

(56) References Cited

U.S. PATENT DOCUMENTS

| | | | |
|---|---|---|---|
| 10,111,994 B2 | 10/2018 | Wu et al. | |
| 10,195,324 B2 | 2/2019 | Foster | |
| 10,201,645 B2 | 2/2019 | Muller | |
| 10,413,648 B2 | 9/2019 | Delgado, III | |
| 10,443,738 B2 | 10/2019 | Durst et al. | |
| 10,722,627 B1 | 7/2020 | Obeid et al. | |
| 11,235,138 B2* | 2/2022 | Gross-Hardt | A61M 60/205 |
| 11,241,569 B2 | 2/2022 | Delgado, III | |
| 11,324,940 B2 | 5/2022 | Earles et al. | |
| 11,351,359 B2 | 6/2022 | Clifton et al. | |
| 11,452,859 B2 | 9/2022 | Earles et al. | |
| 11,471,665 B2 | 10/2022 | Clifton et al. | |
| 11,517,736 B2 | 12/2022 | Earles et al. | |
| 11,571,559 B2 | 2/2023 | Clifton et al. | |
| 11,642,511 B2 | 5/2023 | Delgado | |
| 11,697,017 B2 | 7/2023 | Clifton et al. | |
| 11,745,005 B2 | 9/2023 | Delgado, III | |
| 11,779,751 B2 | 10/2023 | Earles et al. | |
| 11,857,777 B2 | 1/2024 | Earles et al. | |
| 2002/0018713 A1 | 2/2002 | Woodard et al. | |
| 2002/0151761 A1 | 10/2002 | Viole et al. | |
| 2002/0169413 A1 | 11/2002 | Keren et al. | |
| 2003/0105383 A1 | 6/2003 | Barbut et al. | |
| 2003/0144574 A1 | 7/2003 | Heilman et al. | |
| 2003/0176912 A1 | 9/2003 | Chuter et al. | |
| 2003/0233143 A1 | 12/2003 | Gharib et al. | |
| 2004/0044266 A1 | 3/2004 | Siess et al. | |
| 2004/0046466 A1 | 3/2004 | Siess et al. | |
| 2004/0215050 A1 | 10/2004 | Morello | |
| 2005/0131271 A1 | 6/2005 | Benkowski et al. | |
| 2005/0220636 A1 | 10/2005 | Henein et al. | |
| 2006/0036127 A1 | 2/2006 | Delgado, III | |
| 2006/0062672 A1 | 3/2006 | McBride et al. | |
| 2006/0155159 A1 | 7/2006 | Melvin | |
| 2007/0004959 A1 | 1/2007 | Carrier et al. | |
| 2007/0156006 A1 | 7/2007 | Smith et al. | |
| 2008/0103591 A1 | 5/2008 | Siess | |
| 2009/0093764 A1 | 4/2009 | Pfeffer et al. | |
| 2009/0149950 A1 | 6/2009 | Wampler | |
| 2010/0041939 A1* | 2/2010 | Siess | F04D 13/0626 600/16 |
| 2010/0174131 A1 | 7/2010 | Foster et al. | |
| 2010/0249489 A1 | 9/2010 | Jarvik | |
| 2011/0106115 A1 | 5/2011 | Haselby et al. | |
| 2011/0152999 A1 | 6/2011 | Hastings et al. | |
| 2011/0160844 A1 | 6/2011 | Haselby et al. | |
| 2011/0238172 A1 | 9/2011 | Akdis | |
| 2011/0303229 A1 | 12/2011 | Najafi et al. | |
| 2011/0318204 A1 | 12/2011 | Omori | |
| 2012/0029265 A1 | 2/2012 | LaRose et al. | |
| 2012/0134832 A1 | 5/2012 | Wu | |
| 2012/0172654 A1 | 7/2012 | Bates | |
| 2013/0053623 A1 | 2/2013 | Evans et al. | |
| 2013/0303831 A1 | 11/2013 | Evans | |
| 2014/0128659 A1 | 5/2014 | Heuring et al. | |
| 2014/0200664 A1 | 7/2014 | Akkerman et al. | |
| 2014/0275722 A1 | 9/2014 | Zimmermann et al. | |
| 2014/0275726 A1 | 9/2014 | Zeng | |
| 2015/0258260 A1 | 9/2015 | Tuseth | |
| 2015/0285258 A1 | 10/2015 | Foster | |
| 2015/0364863 A1 | 12/2015 | Andrus et al. | |
| 2016/0045652 A1 | 2/2016 | Cornen | |
| 2016/0045653 A1 | 2/2016 | Siess | |
| 2016/0303299 A1* | 10/2016 | Muller | A61M 60/237 |
| 2016/0346450 A1 | 12/2016 | Akkerman et al. | |
| 2017/0014562 A1 | 1/2017 | Liebing | |
| 2017/0043074 A1 | 2/2017 | Siess | |
| 2017/0087288 A1 | 3/2017 | Grob-Hardt et al. | |
| 2017/0188903 A1 | 7/2017 | Bernstein | |
| 2017/0197019 A1 | 7/2017 | Tuseth et al. | |
| 2017/0216507 A1 | 8/2017 | Kushwaha et al. | |
| 2017/0296720 A1 | 10/2017 | Taskin et al. | |
| 2017/0340789 A1 | 11/2017 | Bonde et al. | |
| 2018/0010608 A1 | 1/2018 | LaRose et al. | |
| 2018/0050139 A1 | 2/2018 | Siess et al. | |
| 2018/0050140 A1 | 2/2018 | Siess et al. | |
| 2018/0050142 A1 | 2/2018 | Siess et al. | |
| 2018/0064861 A1 | 3/2018 | Dur et al. | |
| 2018/0154057 A1 | 6/2018 | Garrigue | |
| 2018/0169312 A1 | 6/2018 | Barry | |
| 2018/0193543 A1 | 7/2018 | Sun | |
| 2018/0228953 A1 | 8/2018 | Siess et al. | |
| 2018/0236150 A1 | 8/2018 | Arnold et al. | |
| 2018/0296743 A1 | 10/2018 | Siegenthaler | |
| 2018/0303991 A1 | 10/2018 | Nusser et al. | |
| 2018/0311421 A1 | 11/2018 | Tuseth et al. | |
| 2018/0311425 A1 | 11/2018 | Tuseth et al. | |
| 2019/0001034 A1 | 1/2019 | Taskin et al. | |
| 2019/0060543 A1 | 2/2019 | Khanal et al. | |
| 2019/0097353 A1 | 3/2019 | McSweeney | |
| 2019/0125948 A1 | 5/2019 | Stanfield et al. | |
| 2019/0133599 A1 | 5/2019 | Obermiller et al. | |
| 2019/0143018 A1 | 5/2019 | Salahieh et al. | |
| 2019/0269840 A1 | 9/2019 | Tuval et al. | |
| 2019/0290816 A1 | 9/2019 | Petersen | |
| 2019/0298902 A1 | 10/2019 | Siess et al. | |
| 2019/0328948 A1 | 10/2019 | Salahieh et al. | |
| 2019/0358382 A1 | 11/2019 | Delgado, III | |
| 2020/0121835 A1 | 4/2020 | Farago et al. | |
| 2020/0306434 A1 | 10/2020 | VanCamp et al. | |
| 2020/0316277 A1 | 10/2020 | Delgado, III | |
| 2020/0316278 A1 | 10/2020 | Delgado | |
| 2021/0008264 A1 | 1/2021 | Radman | |
| 2021/0046231 A1 | 2/2021 | Weber et al. | |
| 2021/0052793 A1 | 2/2021 | Struthers et al. | |
| 2021/0060223 A1 | 3/2021 | Weber et al. | |
| 2021/0060224 A1 | 3/2021 | Kronstedt et al. | |
| 2021/0069393 A1 | 3/2021 | Schauer et al. | |
| 2021/0069397 A1 | 3/2021 | Chouinard et al. | |
| 2021/0100940 A1 | 4/2021 | Breidall et al. | |
| 2021/0162196 A1 | 6/2021 | Georges et al. | |
| 2021/0220634 A1 | 7/2021 | Cook | |
| 2021/0220636 A1 | 7/2021 | Schauer et al. | |
| 2021/0220637 A1 | 7/2021 | Edwards et al. | |
| 2021/0260360 A1 | 8/2021 | Georges et al. | |
| 2021/0275796 A1 | 9/2021 | Struthers et al. | |
| 2021/0346680 A1 | 11/2021 | Vogt et al. | |
| 2022/0080179 A1 | 3/2022 | Earles et al. | |
| 2022/0080182 A1 | 3/2022 | Earles et al. | |
| 2022/0080183 A1 | 3/2022 | Earles et al. | |
| 2022/0080184 A1 | 3/2022 | Clifton et al. | |
| 2022/0080185 A1 | 3/2022 | Clifton et al. | |
| 2022/0080186 A1 | 3/2022 | Clifton et al. | |
| 2022/0257920 A1 | 8/2022 | Earles et al. | |
| 2022/0296880 A1 | 9/2022 | Clifton et al. | |
| 2023/0020104 A1 | 1/2023 | Earles et al. | |
| 2023/0060591 A1 | 3/2023 | Clifton et al. | |
| 2023/0256233 A1 | 8/2023 | Clifton et al. | |
| 2024/0017052 A1 | 1/2024 | Delgado, III | |
| 2024/0075275 A1 | 3/2024 | Earles et al. | |

FOREIGN PATENT DOCUMENTS

| | | |
|---|---|---|
| JP | 2014-501554 | 1/2014 |
| JP | 2018-509224 | 4/2018 |
| JP | 2019-523110 A | 8/2019 |
| JP | 2019-530501 A | 10/2019 |
| WO | WO 98/00185 A1 | 1/1988 |
| WO | WO 00/33446 | 6/2000 |
| WO | WO 01/10342 A1 | 2/2001 |
| WO | WO 02/070039 A2 | 9/2002 |
| WO | WO 03/103745 A2 | 12/2003 |
| WO | WO 2005/016416 A1 | 2/2005 |
| WO | WO 2005/020848 A2 | 3/2005 |
| WO | WO 2009/046779 A1 | 4/2009 |
| WO | WO 2009/091968 A1 | 7/2009 |
| WO | WO 2016/146663 A1 | 9/2016 |
| WO | WO 2017/118738 A1 | 7/2017 |
| WO | WO 2017/165372 A1 | 9/2017 |
| WO | WO 2018/096531 | 5/2018 |
| WO | WO 2019/094963 A1 | 5/2019 |
| WO | WO 2019/173596 | 9/2019 |
| WO | WO 2019/229224 | 12/2019 |
| WO | WO 2021/062565 | 4/2021 |

(56) References Cited

FOREIGN PATENT DOCUMENTS

| WO | WO 2021/062566 | 4/2021 |
| --- | --- | --- |
| WO | WO 2021/113389 | 6/2021 |
| WO | WO 2021/117021 | 6/2021 |
| WO | WO 2021/119413 | 6/2021 |
| WO | WO 2021/138673 | 7/2021 |
| WO | WO 2022/256333 | 12/2022 |

OTHER PUBLICATIONS

European Search Report, EP09175307.9, dated Dec. 18, 2009.

Herzum, M. et al., Managing a complication after direct stenting; removal of a maldeployed stent with rotational artherectomy, Heart Jrnl 2005: 91: e46, URL:http://www.heartjnl.com/cgi/content/full/91/6/e46).

Written Opinion of the International Searching Authority, PCT/US2005/028875, Dec. 15, 2005.

International Search report of PCT/US2005/028875, dated Dec. 16, 2005.

Siess, T. et al., "From a lab type to a product: A retrospective view on Impella's assist technology," Artificial Organs, Jan. 15, 2002, vol. 25, Issue 5, pp. 414-421.

Triantafyllou, K.D. et al., Coronary endarterectomy and stent removal with of-pump coronary artery bypass surgery, Heart Journal, Images in Cardiology, dai: 10.1136/hrt.2005.076687, p. 885.

International Search Report and Written Opinion for PCT/US2013/033894, dated Jun. 17, 2013.

International Search Report and Written Opinion for PCT/US2020/062928, dated Apr. 9, 2021, 26 pages.

International Search Report and Written Opinion for PCT/US2020/064489, dated Apr. 8, 2021, 25 pages.

Notice of Allowance mailed Oct. 1, 2021, in U.S. Appl. No. 15/276,590, 14 pages.

Greenberg, B. et al., Rationale, Design and Methods for a Pivotal Randomized Clinical Trial of Continuous Aortic Flow Augmentation in Patients with Exacerbation of Heart Failure: The Momentum Trial, Journal of Cardiac Failure, 2007, vol. 13, No. 9, pp. 715-721.

Vazquez, R. et al., Plasma protein denaturation with graded heat exposure, Perfusion, 2013, vol. 28, No. 6, pp. 557-559.

Extended European Search Report dated Nov. 27, 2023, European Application No. 20896527.7, 6 pages.

\* cited by examiner

| PROTOTYPE | $D_{Hb\_HEUSER}$ | MEAN l |
|---|---|---|
| P_REF | | |
| 18k | 1.0418e-05 | 1.246 |
| 20k | 1.1831e-05 | 1.176 |
| 22k | 1.2514e-05 | 1.105 |
| 25k | 1.3024e-05 | 1.014 |
| P31 | | |
| 18k | 8.6735e-06 | 1.261 |
| 20k | 9.9394e-06 | 1.180 |
| 22k | 1.1531e-05 | 1.107 |
| 25k | 1.2461e-05 | 0.983 |

NON-OCCLUDING INTRA VASCULAR BLOOD PUMP PROVIDING REDUCED HEMOLYSIS

RELATED APPLICATIONS

This application is a continuation of U.S. patent application Ser. No. 15/276,590, filed on Sep. 26, 2016, which claims the benefit of U.S. Provisional Patent Application No. 62/233,025, filed on Sep. 25, 2015, the entire contents of each of which are incorporated by reference.

FIELD OF THE INVENTION

This invention relates to an improved non-occluding intravascular blood pump providing reduced or minimal hemolysis.

BACKGROUND OF INVENTION

Blood pumps may exert stresses on blood that cause hemolysis or blood clotting. A blood pump may provide an inlet, housing, impeller, outlet, and motor. There may be various hotspots in a pump's design of such components that may exert high stress on blood that can cause hemolysis or blood clotting. In addition to health risk associated with hemolysis and blood clotting, these factors may also impair operation of the blood pump. An example of a blood pump can be found in U.S. Pat. No. 8,012,079.

The improved non-occluding intravascular blood pump systems and methods discussed herein reduce and minimize shear forces that can cause hemolysis or blood clotting.

SUMMARY OF INVENTION

In one embodiment, a non-occluding intravascular blood pump comprises a shroud providing an inlet for incoming blood flow and an outlet for outgoing blood flow, wherein the shroud is a cylindrical housing; an impeller positioned within shroud, wherein a central axis of the shroud and impeller are shared; a motor coupled to the impeller, wherein the motor rotates the impeller to cause blood to be drawn through the inlet and output to the outlet, and the motor is centrally disposed and shares the central axis with the shroud and the impeller; and a plurality of pillars coupling the motor to the shroud, wherein the pillars secure the shroud in close proximity to the impeller. The pump may further provide a variety of design features to reduce hemolysis, such as, but not limited to a trumpeted shroud with a larger inlet than outlet; raking back the leading edge of the impeller blades; a large inlet length to reduce turbulent flow prior to the impeller; a large bare hub length; matching the pillar angle to the outlet blade angle; matching flare angles for the impeller base and stator tip; a desired clearance between the shroud and impeller blades, a desired wrap angle, and any combinations thereof.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
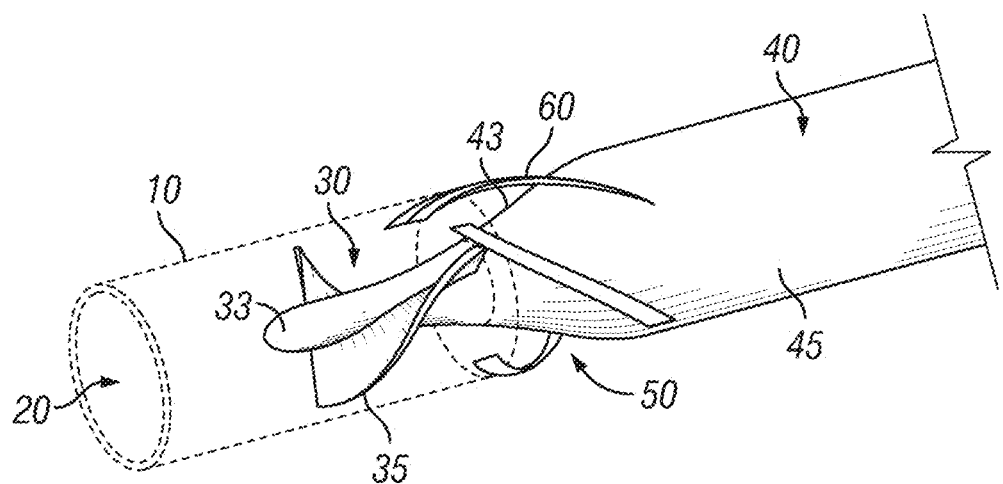
FIG. 1 shows an illustrative example of a blood pump.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

In an improved system, the components of a non-occluding intravascular blood pump are designed to reduce or minimize hemolysis. In some embodiments, the blood pump may be a ventricular assist device or an axial blood pump. In some embodiments, the non-occluding intravascular blood pump may provide a shroud, impeller, and flow stator.

FIG. 1 is an illustrative embodiment of a non-occluding intravascular blood pump. In some embodiments, the non-occluding intravascular blood pump may be an axial blood pump with impeller 30 positioned within a shroud 10. Notably the central axis of the shroud 10 and impeller 30 are shared, and this central axis may be referred to as the central axis of the device or pump as it is shared by several components. A shroud 10 may be a generally cylindrical housing for the impeller 30. The shroud 10 may provide an inlet 20 for incoming blood flow and outlet for outgoing blood flow. The device is described as intravascular because it is designed to operate in a blood vessel of the human body. In some embodiments, the central axis of the pump is roughly aligned with the central axis of the blood vessel. The device is non-occlusive because blood flowing in the blood vessel can flow freely around the device. The impeller 30 is coupled to and rotated by motor 40, which causes blood to be drawn through the inlet 20 and forced out the outlet 50. The motor 40 is also centrally disposed and shares the central axis with the shroud 10 and impeller 30. The impeller 30 may include a hub 33 that is central part of the impeller. The blades or vanes 35 of the impeller 30 may be attached to the hub 33. The motor 40 may include a rotor (not shown), stator 43, and motor body 45. Because the motor 40 is centrally disposed and shares the central axis with the shroud 10 and impeller 30, outgoing blood flow from the outlet 50 is diverted around the motor 40. In order to maintain a desired position relative to the motor 40, the shroud 10 may be coupled to the motor 40 with one or more pillars 60. As the motor 40 is coupled to the impeller 30, the pillars 60 may also secure the shroud 10 in close proximity to impeller. As noted previously above, there are several regions or hotspots of such a device that can create stress that may lead to hemolysis.

Further features of a non-occluding intravascular blood pump are discussed herein for illustrative purposes. Due to the complex interaction of various factors that influence flow it shall be understood that parameters discussed herein are for illustrative purposes only and shall not be construed as limiting examples. Thus, any parameters, such as lengths, diameters, distances, angles, or like for the various components of the device shall be understood to be nonlimiting examples, and such parameters may vary slightly from values discussed below (e.g. +/−10%). It shall also be understood that each of the variety of embodiments discussed herein may be suitable for combination with one or more other embodiments.

Figure 2A:
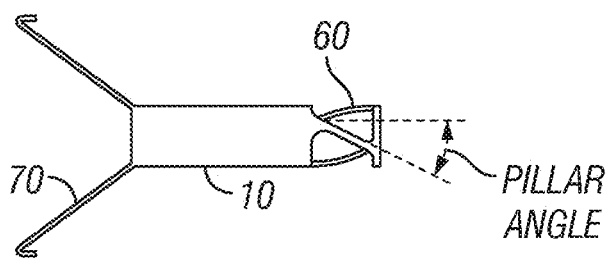
FIGS. 2a-2c show multiple view of an illustrative example of a shroud.
Figure 2B:
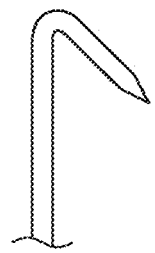
Figure 2C:
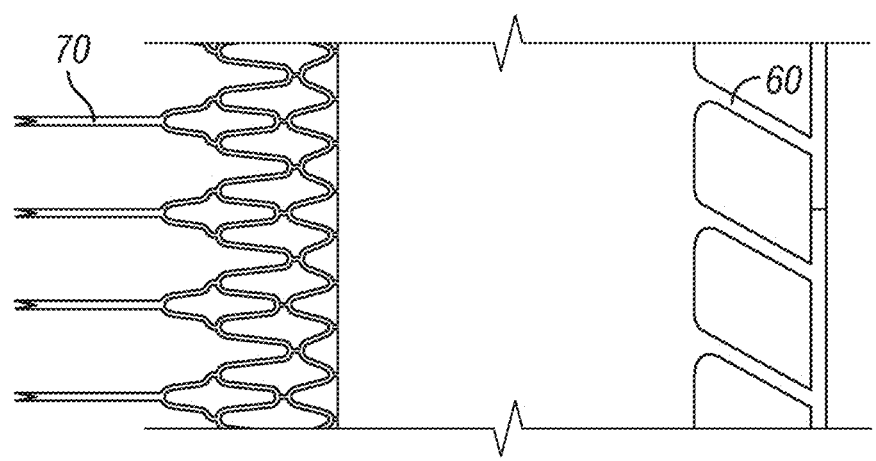

FIGS. 2a-2c show multiple view of an illustrative example of a shroud 10, more particularly, a formed shroud, an enlarged view of a strut tip, and a pre-assembled flat view respectively. In some embodiments, the shroud 10 may be integrated with struts 70 that may be utilized to secure the device in a desired location of the circulatory system in a patient. As shown in the enlarged view of the strut tip, the tip may be hook and pointed to aid secure placement (e.g. Tine bend angle=135°. As shown in the flat view, in some embodiments, the shroud 10 may be formed by patterning (e.g. laser patterning) a desired material to provide struts 70 and pillars 60, and subsequently rolled to form the desired cylindrical shape. The shroud material may be any suitable material (e.g. NiTi or nitinol).

In some embodiments, design aspects of the shroud 10 that are of interest for reducing hemolysis may include the shroud inlet shape. In some embodiments, the shroud 10 may be trumpeted. In particular, the shroud inlet may provide a larger inlet in comparison to the outlet. As a nonlimiting example, the shroud may be trumpeted such that an inlet diameter is larger than an outlet diameter. As discussed further below, this trumpeted design may minimize flow turbulence into the pump at the inlet.

Additionally, various parameters of the shroud 10 may also influence performance, including the shroud inlet length, inlet to blade angle matching, wrap angle, or combinations of these various parameters. In some embodiments, a shroud inlet length is long enough to prevent turbulent flow detachment. The shroud inlet length is defined as a length from the inlet to a tip of the impeller. In some embodiments, the necessary length may be a function of the shroud diameter, the inlet blade angle, the wrap angle, and/or impeller speed. As a nonlimiting example, in the embodiment explored, a shroud inlet length of 9 mm or greater was sufficient to prevent detachment. In some embodiments, a shroud inlet length of at least 1.5 times the inner diameter of the shroud is sufficient to provide good flow conditions for the impeller. In some embodiments, a shroud inlet length of at least 0.5 times the inner diameter of the shroud is included to be sufficient to provide good flow conditions for the impeller. In some embodiments, a shroud inlet length of 0.5 to 1.5 times the inner diameter of the shroud is included to be sufficient to provide good flow conditions for the impeller. Optimal dimensions may depend on native flow conditions.

Figure 3A:
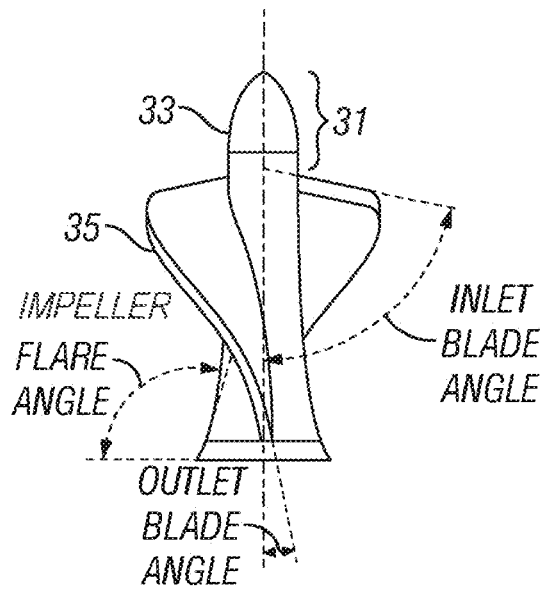
FIGS. 3a-3c show multiple view of an illustrative example of an impeller.
Figure 3B:
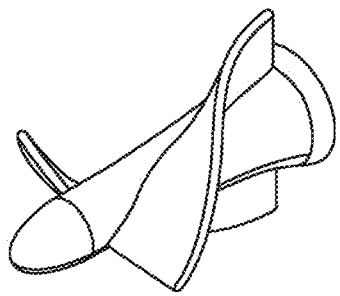
Figure 3C:
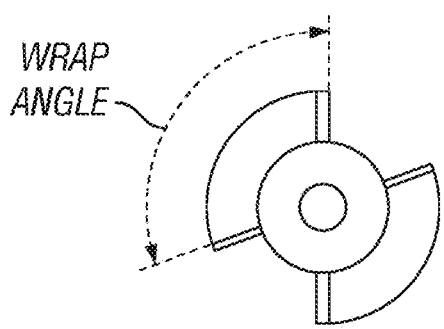
Figure 4A:
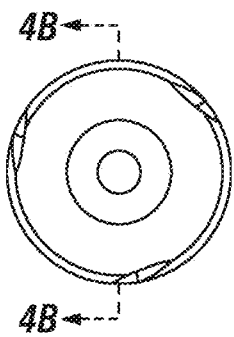
FIGS. 4a-4e show multiple view of an illustrative example of a stator.
Figure 4B:
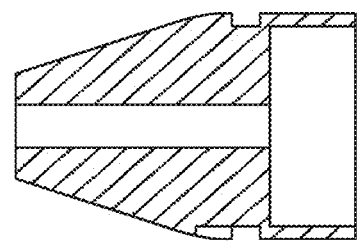
Figure 4C:
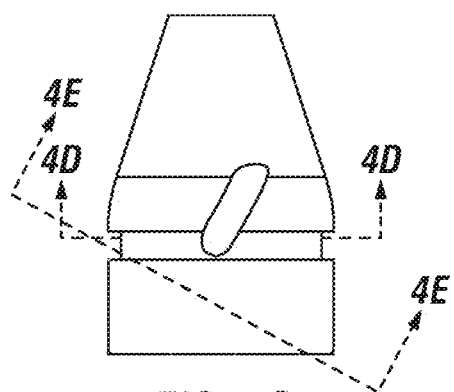
Figure 4D:
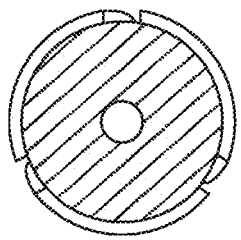
Figure 4E:
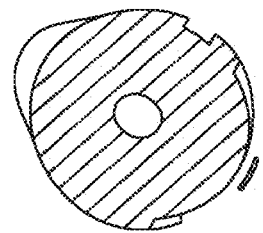
Figure 5A:
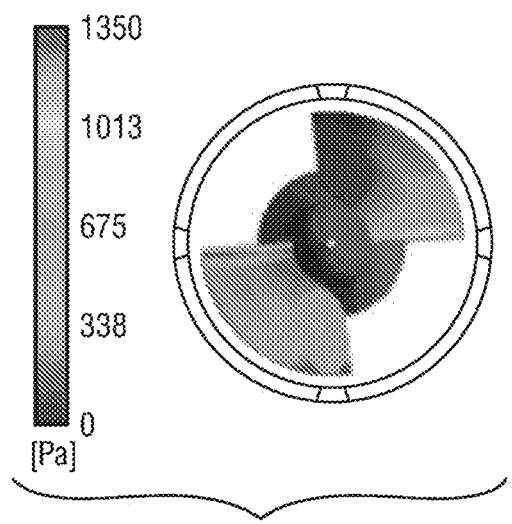
FIGS. 5a-5f show hotspots for various components of the pump.
Figure 5B:
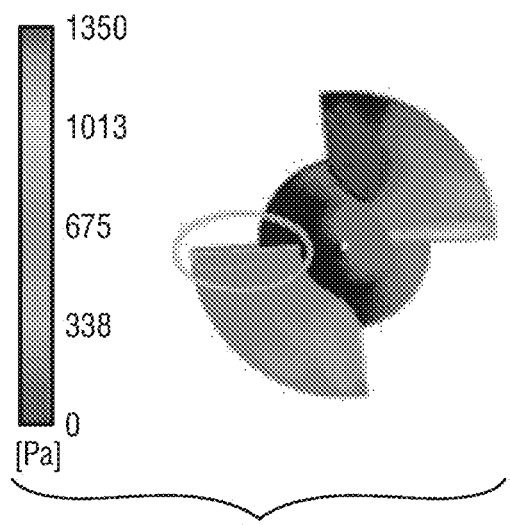
Figure 5C:
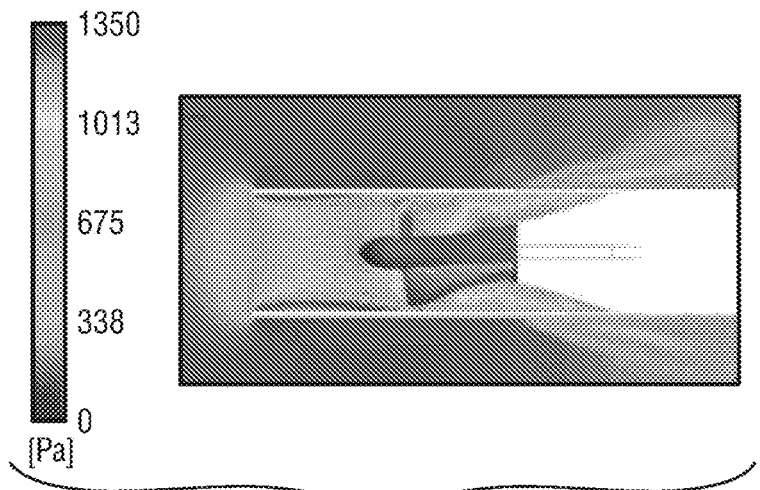
Figure 5D:
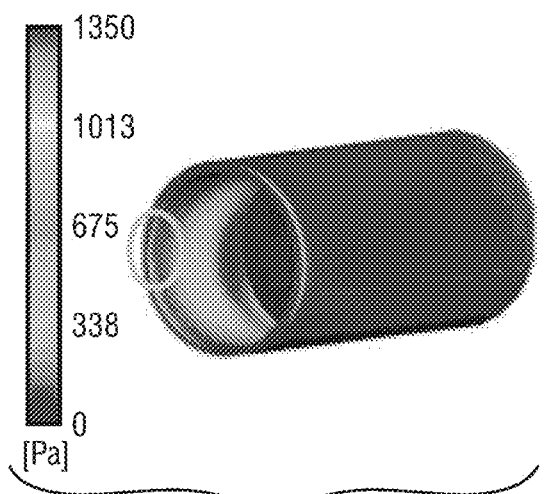
Figure 5E:
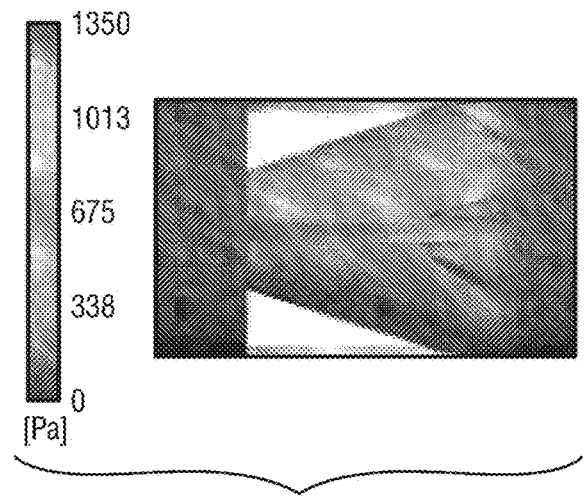
Figure 5F:
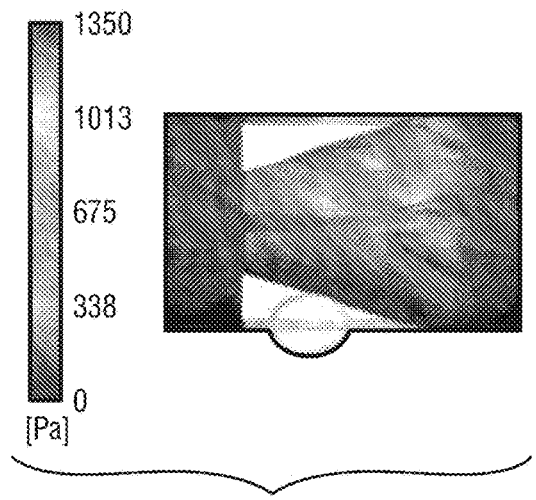

FIGS. 3a-3c show multiple view of an illustrative example of an impeller. More particularly, a side view, isometric view, and top view of the impeller. As discussed previously, the impeller is positioned on the central axis of the pump and rotates about the central axis when driven by the motor. The hub 33 refers to the central portion of the impeller and may be selected from any suitable blunted or truncated cone design (e.g. spherical, elliptical, parabolic, etc.) The bare hub or hub tip 31 is a portion of the tip of the impeller before blade attachment or a length from the tip of the hub 33 to the beginning of the blades 35. The length of the hub tip 31 should be selected to provide beneficial flow results. In some embodiments, a long hub tip 31 is selected to provide laminar flow to the impeller inlet domain area. The necessary length and shape of the bare hub 31 may depend on the inner shroud diameter, the inlet blade angle, the wrap angle, and/or impeller speed. In some embodiments, a bare hub length of at least 0.3 times the inner diameter of the shroud may be sufficient to provide good flow matching between the inlet flow and the impeller. In some embodiments, a bare hub length of at least 0.2 times the inner diameter of the shroud may be sufficient to provide good flow matching between the inlet flow and the impeller. In some embodiments, a bare hub length of 0.2 to 0.3 times the inner diameter of the shroud may be sufficient to provide good flow matching between the inlet flow and the impeller. In some embodiments, the bare hub length embodiments discussed herein may be combined with embodiments discussing the shroud inlet length. The inlet blade angle refers to angle of the leading edge of the blade 35 relative to the central axis when measured from the downstream side. It is apparent from figures that the leading edge is the edge of the blade closest to the inlet. In the embodiment explored, a bare hub length of roughly 2 mm, with proper profiling, was sufficient to provide good flow conditions. The wrap angle refers to an angle occupied by a single blades 35 wrapped around the hub when viewed from the perspective of the central axis or an angle around the central axis that the single blade occupies (e.g. FIG. 3c). In some embodiments, the wrap angle may be 100+/−10 degrees.

In some embodiments, the leading edges of the blades 35 may be raked back and/or may be sharp, pointed, rounded, or the like. Traditional pumps arrange the leading edge of vanes to extend directly perpendicular to a central axis of the pump. In other words, the leading edges of the impeller vanes typically come straight out from the central axis of the pump or the inlet blade angle of typical impeller vanes is 90°. In some embodiments, the leading edge(s) of the impeller vanes are raked back with respect to the direction of flow so that an inlet blade angle (or leading edge angle or rake angle) between the central axis and leading edge is less than 90° (measured from the downstream side of the leading edge). The proper inlet blade angle may depend on the length and shape of the bare hub and the speed of the pump. In some embodiments, the leading edge(s) of the impeller vanes are raked back so that the leading edge angle is ≥60° and <90°. In certain embodiments, the rake angle should be in the range of 75-85 degrees. In some embodiments, the leading edge(s) of the impeller vanes are raked back more so that an angle between the central axis and leading edge is 60-75 degrees. In some embodiments, the leading edge(s) of the impeller vanes are raked back more so that an angle between the central axis and leading edge is less than 60°.

Referring to FIGS. 2a-2c and 3a-3c, the shroud and impeller may be matched. In some embodiments, the shroud-tip clearance or a clearance between the inner surface of the shroud and the vanes 35 of the impeller may be designed to be in a desired range. Necessary clearance values may be related to design tolerances, the diameter of the impeller, and the speed of the pump. As a nonlimiting example, clearances may be set to maintain shear rates below a critical value of 10,000-50,000 $s^{-1}$. For some embodiments, the clearance distances should be at least 250 microns (+/−50 micron). In some embodiments, the clearance between the interior surface of the shroud and the blades of the impeller may be between 200 microns to 300 microns.

FIGS. 4a-4e show multiple view of an illustrative example of a stator, which is the stationary part of a motor. In some embodiments, the stator and impeller may be matched. In some embodiments, flaring of stator hub or slope of the stator hub is selected to match the flare at the base of the impeller or the impeller flare angle may be approximately equal to the stator flare angle. An impeller flare angle is an angle between the outer surface of the base of the impeller and line perpendicular to the central axis (e.g. FIG. 3a). A stator flare angle is angle between the outer surface of the tip of the stator and line perpendicular to the central axis (e.g. FIG. 4b). In some embodiments, the base diameter of the impeller and tip diameter of the stator hub may be approximately equal. In some embodiments, the impeller flare angle may be approximately equal to the stator flare angle, and the base diameter of the impeller and tip diameter of the stator hub may be approximately equal. This provides a smooth transition between the impeller and stator that minimizes disruption in flow.

Referring to FIGS. 2a-2c and 3a-3c, the pillars 60 and impeller may be matched. As shown in FIG. 2a, a pillar angle is an angle between the pillar 60 and the central axis of the pump. In some embodiments, the pillar angle is non-zero. Referring to FIG. 3a, the blade angle or outlet blade angle is an angle of the trail end of the blade relative to the central axis. In some embodiments, the pillars may be curved to match the outlet blade angle to minimize shear stress and resistance and optimize flow path. Due to the complex interaction of various factors that influence flow, the optimal angle move +/−5-10 degrees from an exact matching angle.

In some embodiments, the number of pillars compared to the number of impeller blades may be selected to mismatch. For example, a non-integer ratio of impeller blades to pillars may be selected so that they are not equal or matched. In some embodiments, the alignment of the pillars relative the impeller blades may be selected to mismatch, and may optionally combined with the above noted mismatching of the number of pillars and blades. For example, in a nonlimiting embodiment, the pillar and blade configuration may be selected so that when at least one blade is aligned with one of the pillars, the other remaining blades are not all aligned with the other remaining pillars. For example, three outlet pillars may be provided when two impeller blades are provided. In some embodiments, the pillars may be irregularly spaced. In some embodiments, pillar and blade configurations are selected so that when at least one blade is aligned with one of the pillars, none of the remaining impeller blades align with any of the remaining pillars.

In some embodiments, the device may be a catheter-based circulatory heart pump, such as a pump designed specifically for NYHA Class III-IVa heart failure patients who are too sick for medication alone, but not sick enough for risky surgical interventions (i.e. LVAD or transplant).

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure. It should also be noted that the examples discussed below progressed through various phases of testing where the designs remained confidential, as such earlier design phases should not be construed as known prior art.

Some of the challenges in producing an improved non-occluding intravascular blood pump are the numerous design factors that can influence performance. It was found that the best approach to get a feasible design includes seeking a minimally invasive design, high rotational speeds, and adaptation for wide operational range. Detailed flow analysis was performed, particularly transient analysis, which allowed precise prototype comparison and setup. Further discussion below includes discussion of typical hotspots, geometry iterations for impeller and housing, results, and conclusions, including hotspot analysis that enables efficient shear force and hemolysis reduction.

The project progressed through three project phases with the initial phase starting with a basic pump design utilized to identify common design flaws causing hemolysis. Initial challenges of the experiments, particularly project Phase 1 and 2, were to develop hydraulic design, including ~6 mm diameter pump, placement in the descending aorta, and in series operation with the left ventricle. Further, additional goals were to deliver sufficient hydraulic output to increase circulation and decrease the workload of the native heart. Phase 3 goals included achieving the lowest hemolysis possible, while providing a wide off-design operating range, lower speeds, and delivering adequate hydraulic output.

Evaluation strategy included simulation in (physiological) operation environment with validation through pump h-q curves and pressure gradient driven backflow. Pump flow depends strongly on rpm and slightly on output flow & pressure.

The Numerical Setup included simulation of series operation, placement in the descending aorta, pump flow function (rpm), validation of pump performance, hotspot analysis of impeller, including asymmetrical shear pattern, flow exploration in inflow shroud, including turbulent flow detachment, and pillar geometry. FIGS. 5a-5f show hotspots for various components of the pump.

Figure 6:
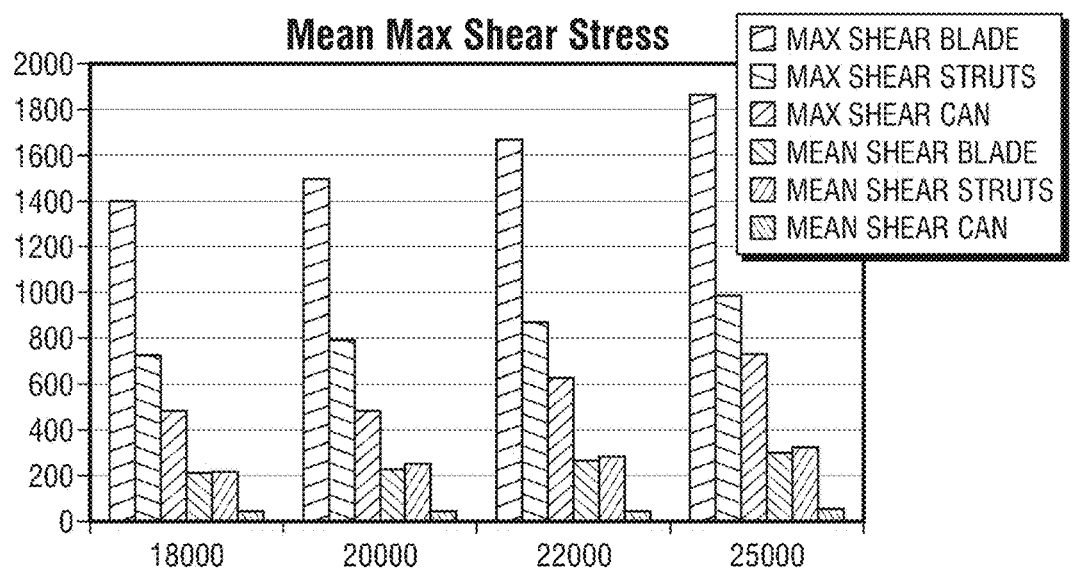
FIG. 6 show mean/max sear stress for the shroud, blade and pillars.

In order to identify the greatest potential for optimization without sacrificing performance, shear stress hotspot identification was performed. Major localized hotspots were found at the impeller, inflow shroud, and pillars. Pre-analysis included hotspot component quantification. FIG. 6 show mean/max shear stress for the shroud, blade and pillars. It was noted that max shear: Impeller>>Pillars>Shroud, and mean shear: Impeller~Pillars>>Shroud. Operational range analysis included hotspot screening for wide operation range, particularly for constant speed, imposed mass flows, as well as localized hotspots.

Figure 7:
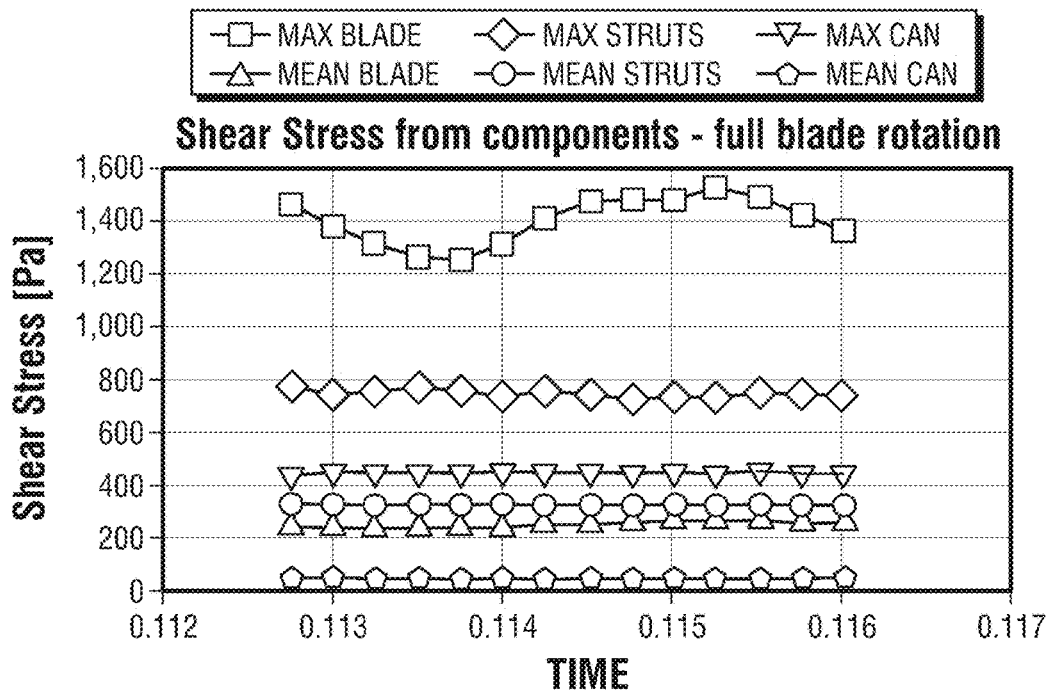
FIG. 7 shows max/mean shear stress for the blade, pillars, and shroud over time.

Prior to the experiments, it was unclear what provokes the asymmetrical shear pattern at the impeller leading edge. An unexpected result was that the detached flow reached as far as the impeller leading edge and provoked the patterns. Transient data was also analyzed to extend the analysis setup. FIG. 7 shows max/mean shear stress for the impeller, pillars, and shroud over time. Transient results were indispensable for optimization, and allowed comparison of mean value and deviation for different designs and identification of geometry flaws that provoke turbulent flows.

Operational range analysis was performed for hotspot screening to determine component contribution to maximum shear stress, shear stress for various rpms, and shear stress for impeller rotation.

Testing showed certain design features may result in improvement:
  Inlet Shroud: an elongated shroud demonstrated the same detachment and symmetric shear at impeller. A smooth inlet transition reduced detachment length of incoming flow at the inlet.
  Impeller: On the upstream portion of the impeller, parameters of interest included the bare hub length. Where the impeller blades join the hub, parameters of interest include leading edge angle and shape (or roundness). Along the bladed portion of the impeller, the parameter of interest was the wrap angle (or blade extent). At the downstream edge of the impeller blades, the parameter of interest was the trailing edge angle or outlet blade angle.
  Outflow Pillars: It was found that edge shape rounding and adjusting pillar tilt angle according to pump outflow angle were important.

Analysis at different scales provided complimentary results. Local prediction showed improved impeller blade surface smoothness resulted in a reduction of maximum (150-200 Pa) and mean shear stress for various RPMs. Global prediction and hotspot analysis enabled improved overall numerically predicted damage index (include time exposure). The analysis show overall improvement for the intended operating range.

Figure 8:
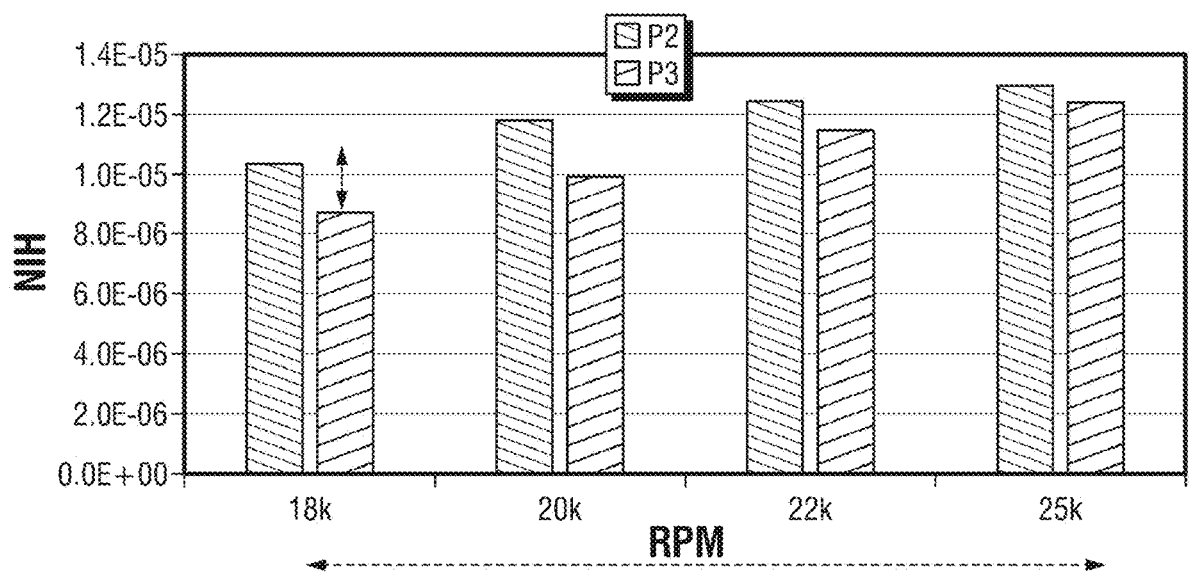
FIG. 8 show the NIH for various rpm for P2 and P3.
Figure 9:
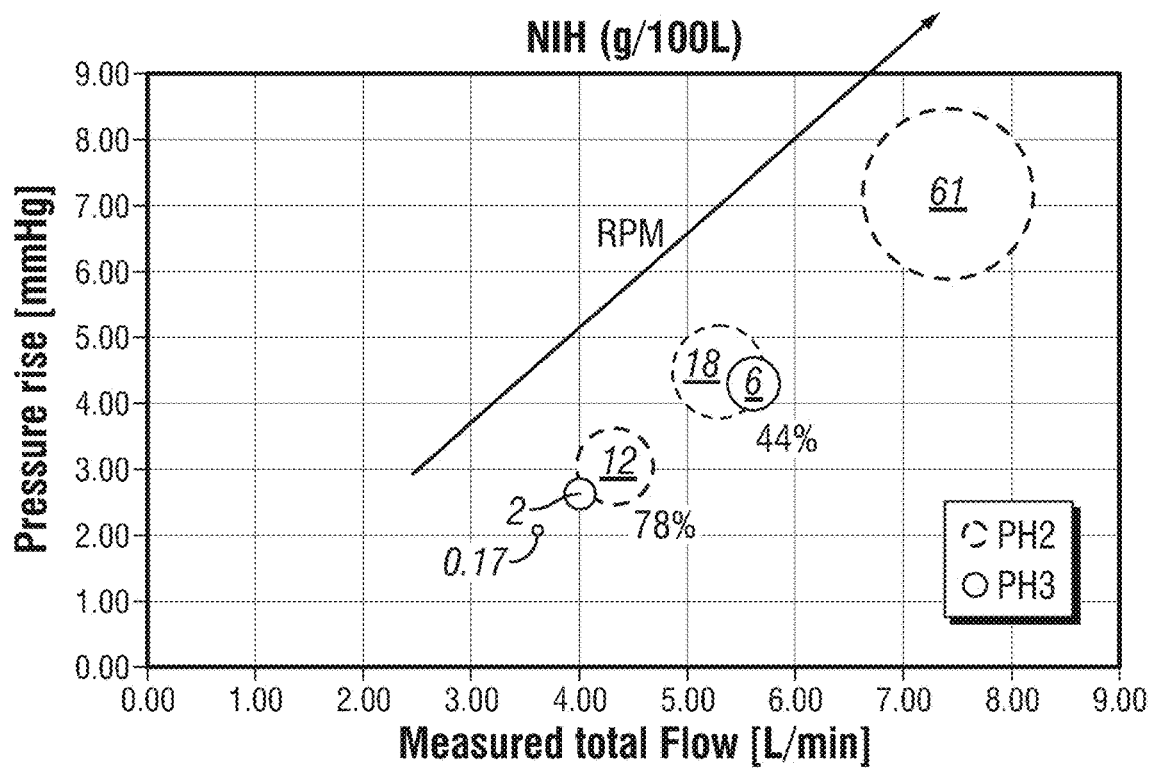
FIG. 9 shows pressure rise v. NIH and measure total flow.

Experimental NIH validation: FIG. 8 shows the NIH for various RPM for P2 and P3, and FIG. 9 shows pressure rise v. NIH and measured total flow. Hotspot analysis enabled improved overall numerically predicted damage index AND experimentally found levels of hemolysis. Experiments show greatly improved hemolysis results as a multiple of BP80 reference pumps.

Conclusion: Thorough hot spot analysis to determine optimization procedures allows one to identify the possible interplay of hotspots, and decide on optimization order(s) to achieve a wide operation range and improved hydraulic output.

The non-occluding intravascular blood pump discussed herein is a minimally invasive continuous axial flow pump (e.g. ~6 mm width) and is especially suited for New York Heart Association (NYHA) Class III and early IV patients. The miniaturization of a pump of this type requires high rotational impeller speeds to achieve sufficient unloading of the heart. In order to minimize hemolytic potential of the blood contacting components, a detailed analysis was conducted and iterative optimization of the geometry to design a prototype impeller and blood contacting components. Transient computational fluid dynamic (CFD) simulations over multiple impeller rotational speeds were conducted to determine the time dependent exposure to shear stress, shear stress hotspots, and individual component contribution to hemolysis. The shape of the pump components were iteratively changed to optimize the local flow and shear stress exposure. The final prototype configuration was further numerically evaluated using a conventional Lagrange particle tracking approach accounting for the blood damage accumulation. For validation, in vitro hemolysis testing and flow loop pump performance was conducted. Compared to the initial design, reduction in shear stress and mitigation of hotspots could be achieved. Maximum shear stress exposure could be reduced by 150-200 Pa For the impeller, and average shear on the impeller surface was reduced below 400 Pa up to 30,000 rpm impeller speed. Experimental results of the pump's Normalized Index of Hemolysis (NIH) values showed a significant improvement of 78% at the desired operating speed of 20 k rpm, showing a comparable NIH Level range as the reference pump BP80. Flow Loop performance testing verified that flow rate and pressure generation was maintained following the design changes that resulted in reduction of hemolytic potential. The new prototype features lower numerically predicted and experimentally verified hemolytic potential and increased efficiency through improved overall flow guidance.

In Phase III, a complete analysis of shear stress hotspots within the pump and their individual contribution to hemolysis was conducted. The main focus of this study is the optimization towards lowest possible hemolysis potential by iteratively adapting the blade shape. Furthermore, the whole pump is analyzed for further shear stress hotspots. After identification of the existing shortcomings in the actual prototype impeller operating at the chosen speed range, several shroud and pillar designs are explored. A vast number of different geometries have been created, simulated and analyzed to determine the optimal geometry component fit.

Figure 10:
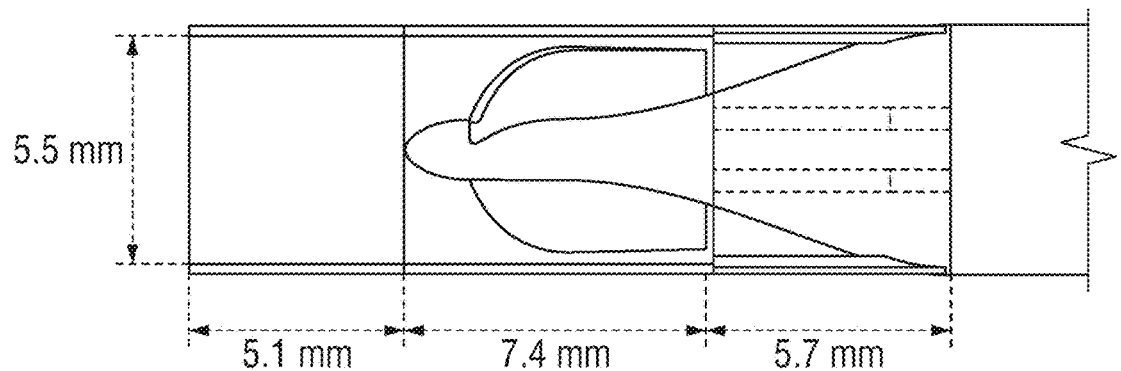
FIG. 10 shows the phase 2 prototype's configuration.

Current Prototype from Phase II: The current prototype (or P_ref) has been identified in an extensive optimization in phase II to lower overall hemolysis potential. FIG. 10 shows the phase 2 prototype's configuration. At that time, the optimal impeller speed was determined to be at 32 k rpm and a significant optimization could be achieved.

P_ref has been evaluated in several hemolysis tests. The main changes conducted in phase II were the iterative adaptation of inlet and outlet blade angle to achieve an overall better flow guidance of the impeller, as well as an increase in wrap angle which allowed a better flow guidance within the blade passage. Furthermore, the shape of the tip hub section has been altered to allow for a more evenly distributed and laminar flow pattern at the impeller inlet region. In the following discussion the further geometry changes to decrease the hemolytic potential of the hotspots identified are presented.

Shroud: An efficient and reliable pump is achieved by a targeted tuning of its components to one another. A perfect example of this was experienced during this study. The shroud length does not significantly lower the shear stress for the component shroud, but eliminates the dependence of blade rotation angle and turbulent flow features on impeller shear stress distribution. The extension of the shroud is necessary to avoid detached turbulent flow reaching into the impeller inlet domain area. This turbulent flow is responsible for the asymmetrical impeller shear stress load and, due to its turbulent random nature, impedes a significant and conclusive optimization of the blade. The results show the impact of detached flow on the shear stress values by having huge oscillation around its mean.

Figure 11:
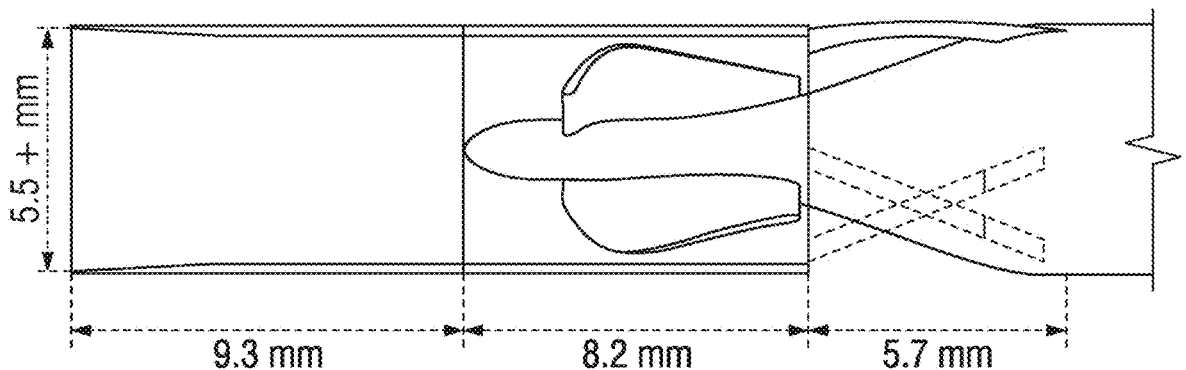
FIG. 11 shows an improved design with geometry data.
Figure 12A:
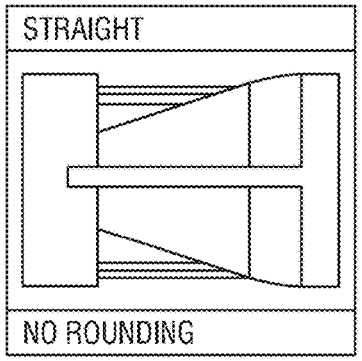
FIGS. 12a-12f shows selected pillar geometries.
Figure 12B:
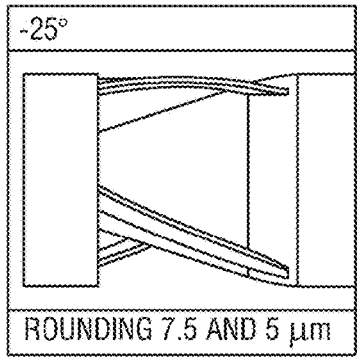
Figure 12C:
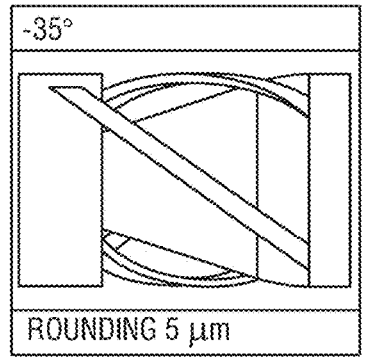
Figure 12D:
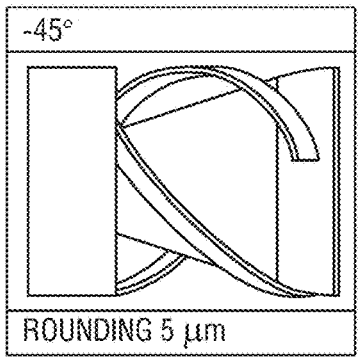
Figure 12E:
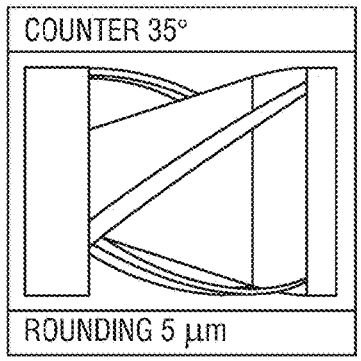
Figure 12F:
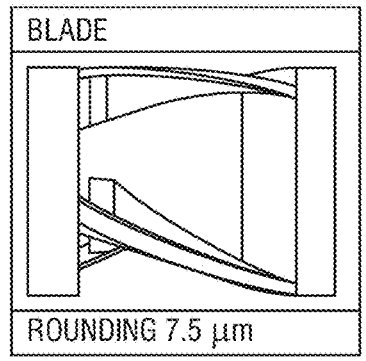
Figure 13A:
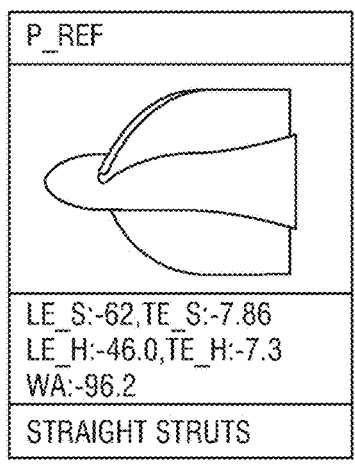
FIGS. 13a-13f shows selected impeller geometries.
Figure 13B:
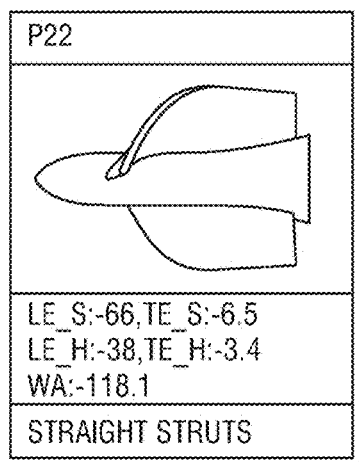
Figure 13C:
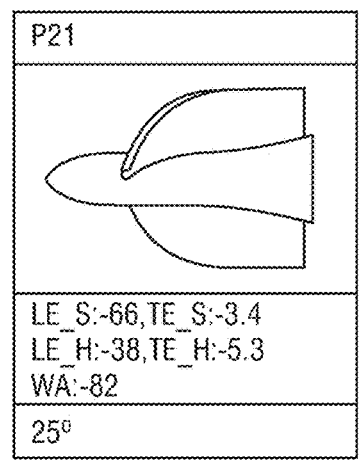
Figure 13D:
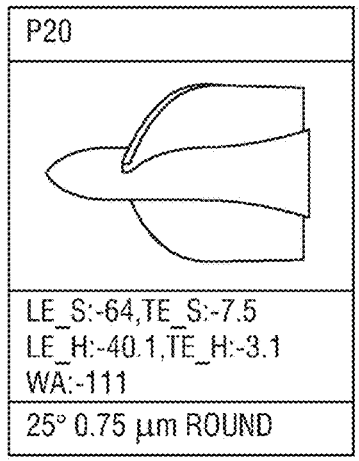
Figure 13E:
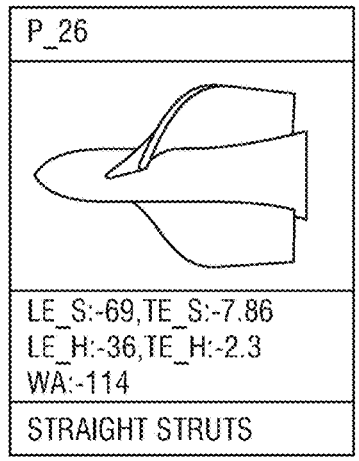
Figure 13F:
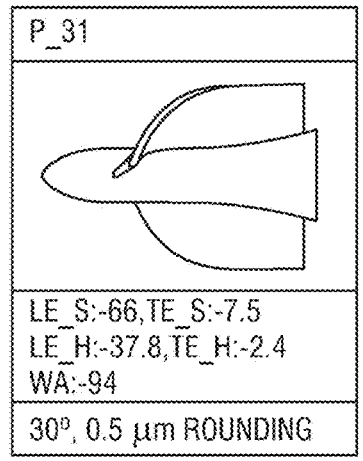
Figure 14A:
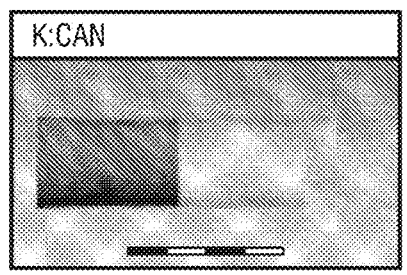
FIGS. 14a-14d show the individual components and the test surface area evaluated for max and mean shear stress.
Figure 14B:
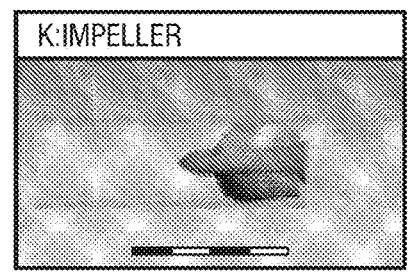
Figure 14C:
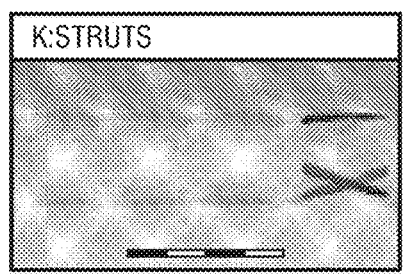
Figure 14D:
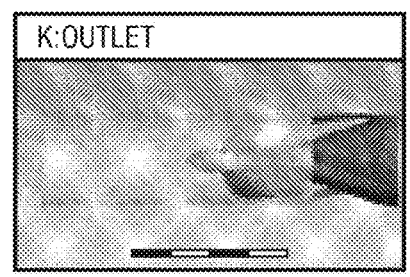

During Phase III, the shroud has therefore been extended; exact data can be found in FIG. 6. FIG. 11 shows an improved design with geometry data. These considerations suggest that an improved pump by extending the shroud length or inlet pipe to allow for sufficient flow settlement, e.g. at least 9.3 mm for the prototype. This can be generalized as at least 1.5 times the shroud inner diameter. Further, a trumpet shape at the inlet is preferred in terms of even earlier flow settlement.

Pillars: The setup from FIG. 11 has been further extended to also record statistics for shroud and pillar stress to capture all shear stresses occurring during 2 blade rotations. Various pillar designs have been modeled and simulated and are explained below. FIGS. 12a-12f shows selected pillar geometries. The basic idea behind modification of the pillar design is to align the pillars in direction of the outflow jet to minimize the surface area that is directed towards it.

Two main considerations need to be discussed. Due to the orientation of the pillars, the location of the hotspots is affected. A highly twisted pillar design will move the hotspot in the direction of the transition of pillar to motor. In addition, it is assumed that a better aligned pillar compromises less attack surface area and thus reduces the average load. Furthermore, two designs have been created. A counter oriented pillar design at 35°, as well as a stator-pillar component to assess maximum occurring shear stress in relation to mean shear stress.

Impeller: Fifteen independent pump geometry combinations have been simulated to identify the best possible designs and combination. FIGS. 13a-13f shows selected impeller geometries. Next to the iterative adaptation of the blade angles along the leading edge, a further elongation of the hub showed beneficial impact on changes made to the blade angles. Furthermore, for the same leading edge blade angles, the impact of wrap angle has been investigated as well as with reference to the hub inclined leading edge.

Blood Damage Prediction: Shear-induced blood trauma (hemolysis) is estimated by computing the damage accumulation along 3000 particle path lines using a Lagrangian particle tracking technique and applying a power-law empirical damage model as suggested by Heuser:

$$D_i = C \times \tau^\alpha \times t^\beta$$

where Di represents the blood damage index for each particle, C, α and β denote constants originally specified by Giersiepen and later corrected by Heuser as $$C=1.8\times10^{-6}, \alpha=1.991, \text{ and } \beta=0.765.$$

As these coefficients are derived from uniform-shear experiments in Couette-type flow, there are certain limitations to the current problem. However, it is assumed that this does not affect the comparative evaluation of similar pumps. To account for the highly time-variant shear history of blood cells through the pump, the cumulative damage is estimated by the method extended to blood pumps by Bludszuweit (1) based on the assumption of linear accumulation of shear at different loading levels:

$$D_{Hb} = \frac{1}{n}\Sigma_{inlet}^{Outlet} D_i$$

where n is the number of total particles released in the pump inlet, and Di is calculated using the proposed constants by Heuser. Because of the three-dimensional character of the shear field, the Von Mises stress provides a representative scalar norm for use in calculation of $D_i$, as proposed by Bludszuweit:

$$\tau = \left[\frac{1}{6}\Sigma(\tau_{ii} + \tau_{jj})^2 + \Sigma\tau_{ij}^2\right]^{\frac{1}{2}}$$

where the components of the stress tensor were computed from the summation of the components of the viscous and Reynolds stress tensor.

Results: In the course of this project, a huge data set by the evaluation of all configurations prototype was created. To an illustrative comparison, however, only the parameters of comparison of the original and within this project identified final pump geometry are shown below. Furthermore, most graphic results are shown at 20 krpm. Due to the huge amount of created data, only selected configuration results will be shown below. The individual components and the test surface area evaluated for max and mean shear stress are shown in FIGS. 14a-14d. Surface area K:OUTLET was monitored for every run to make sure that modifications made to the pillars do not somehow impair the shear stress distribution in the whole outlet area of the pump.

Figure 15A:
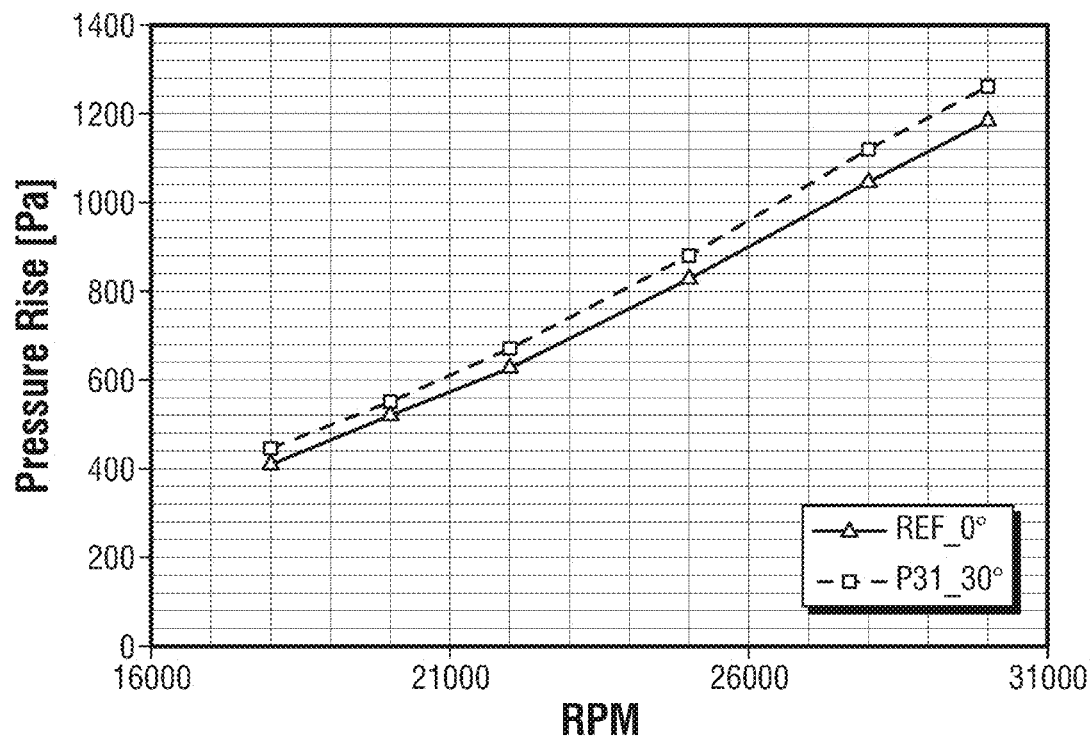
FIGS. 15a-15c show hydraulic output results, or more particularly, pressure rise, pump flow and shaft relative to rpm for Ref_0 and P31_30.
Figure 15B:
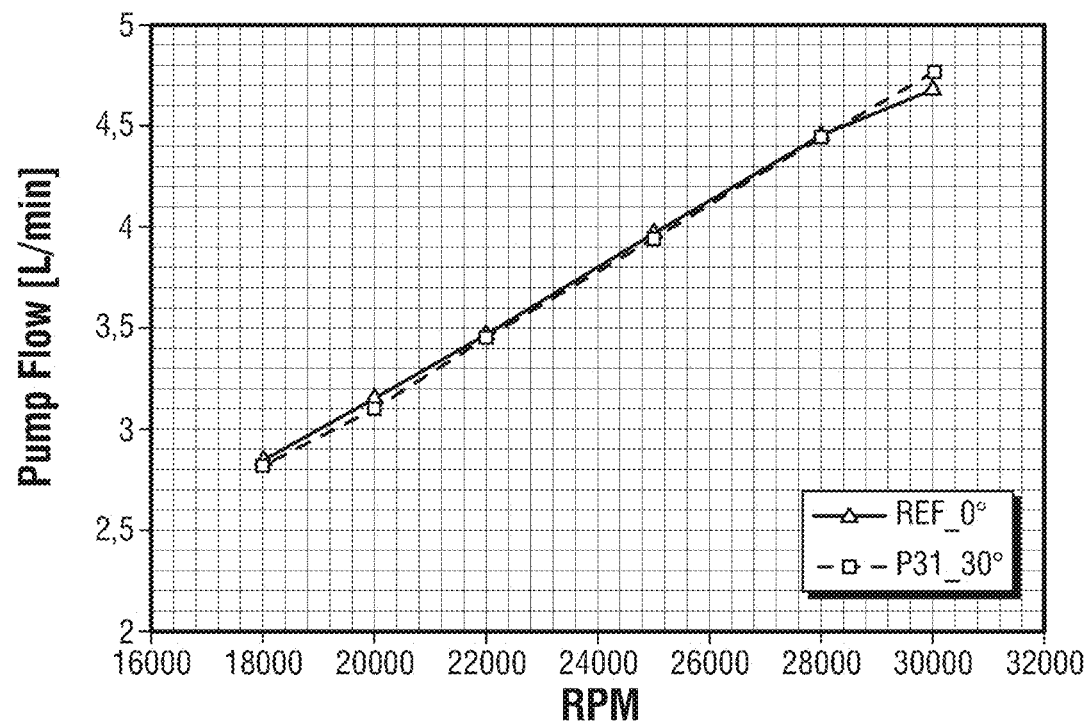
Figure 15C:
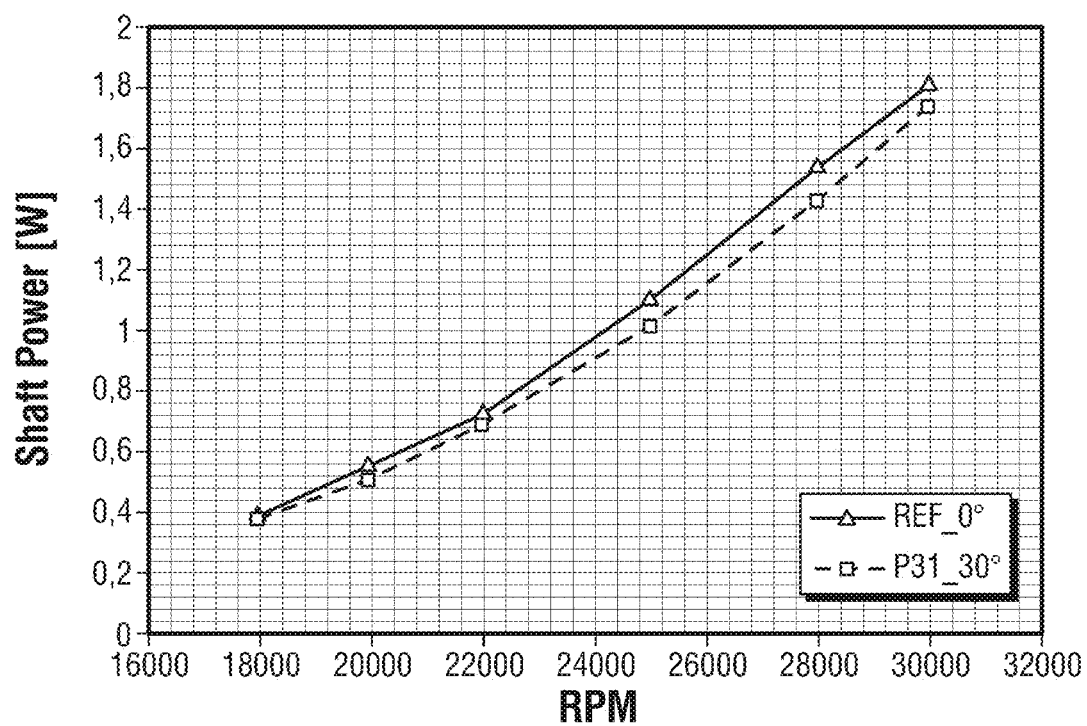

A necessity for any proposed geometry modification in this study is the maintenance of sufficient hydraulic output. The modifications on the impeller blade to achieve a lower hemolytic potential were strictly monitored and compared to the desired hydraulic output. A small increase in hydraulic output was achieved while lowering the necessary impeller shaft power. This yields in an overall better pump efficiency. FIGS. 15a-15c show hydraulic output results, or more particularly, pressure rise, pump flow and shaft relative to rpm for Ref_0 and P31_30.

Figure 16A:
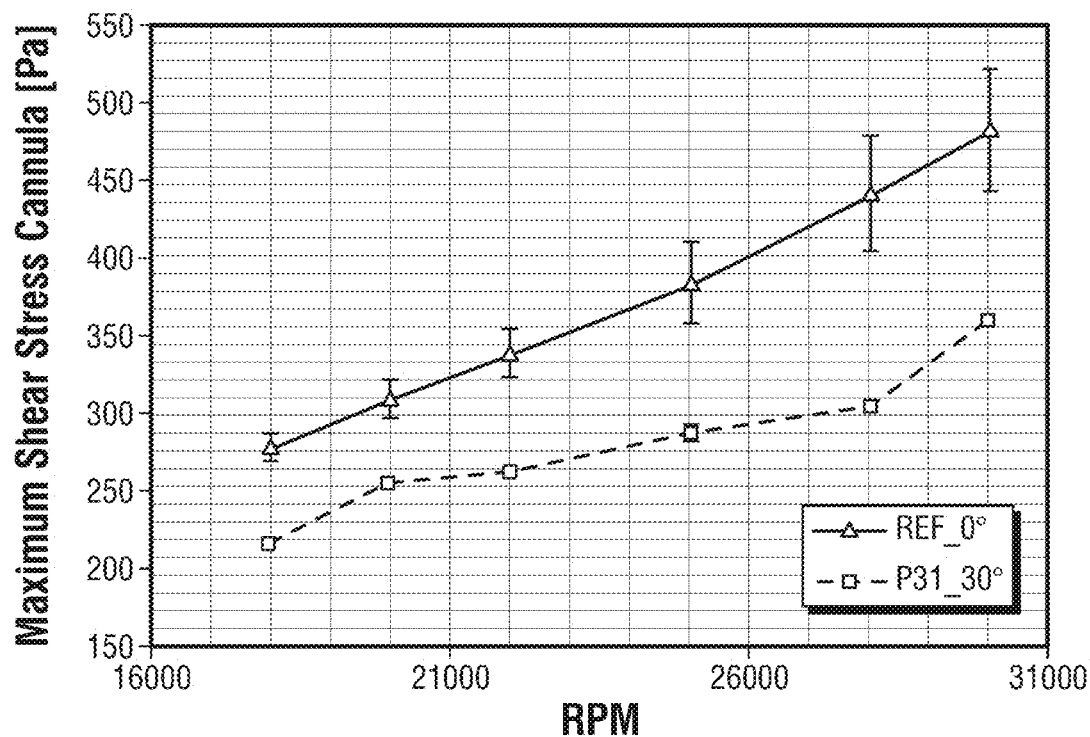
FIGS. 16a-16b show the maximum and mean shear stress for the reference and P31 design
Figure 16B:
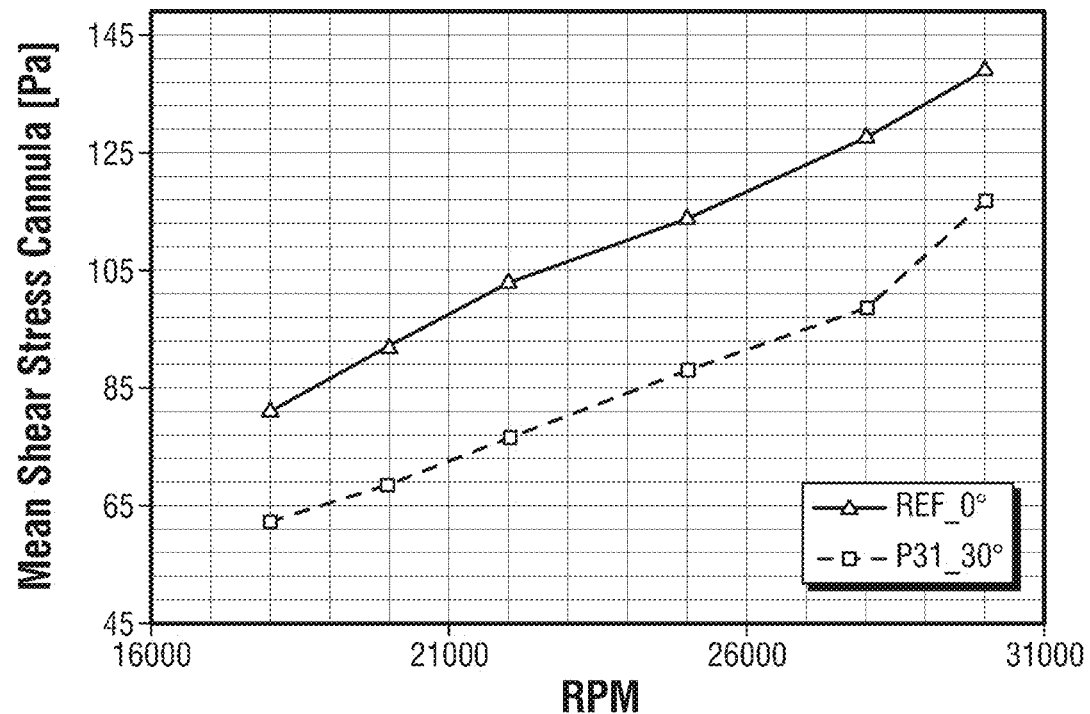

Shroud: The results for the shroud show how both maximum and mean shear stress could be lowered from the reference to the proposed design P31. FIGS. 16a-16b show the maximum and mean shear stress for the reference and P31 design. A significant offset could be achieved.

It can be argued, that the extension of the shroud also increased the surface area over which the mean values are derived.

Figure 17A:
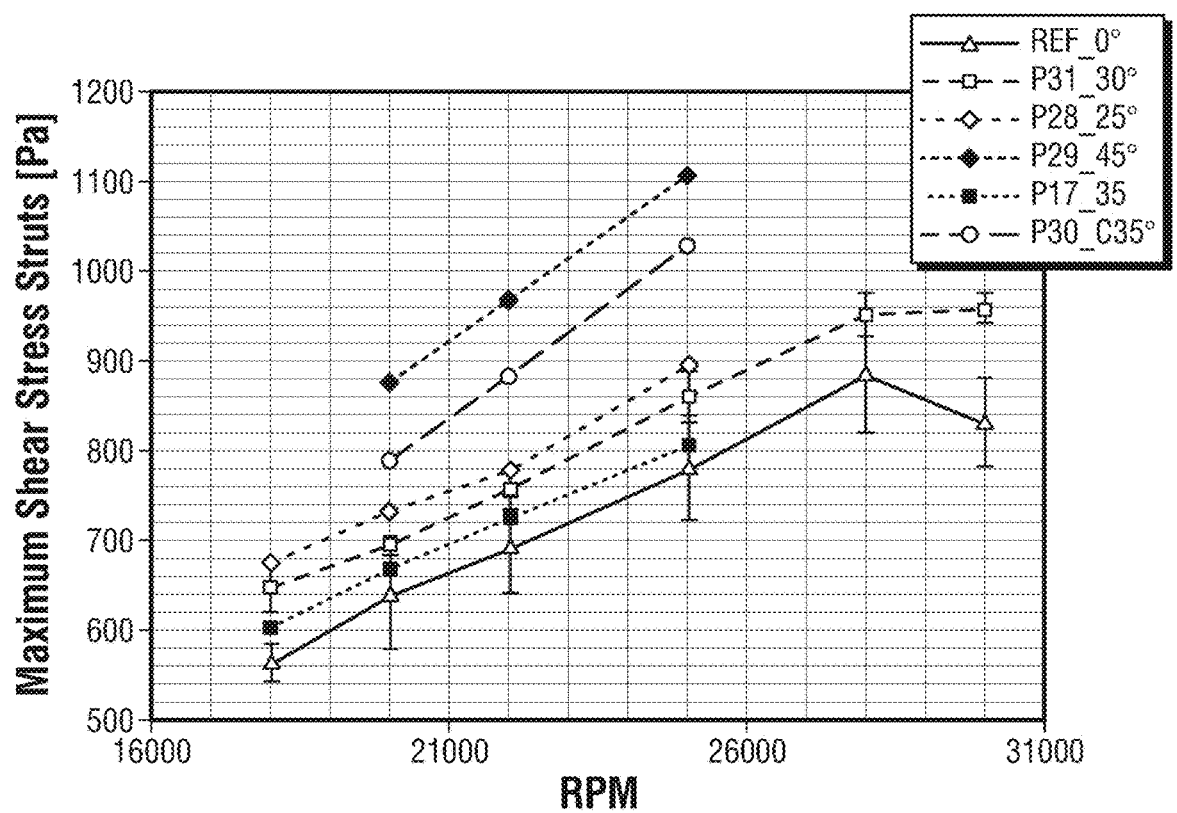
FIGS. 17a-17b show the maximum and mean shear stress for the reference and P31 design.
Figure 17B:
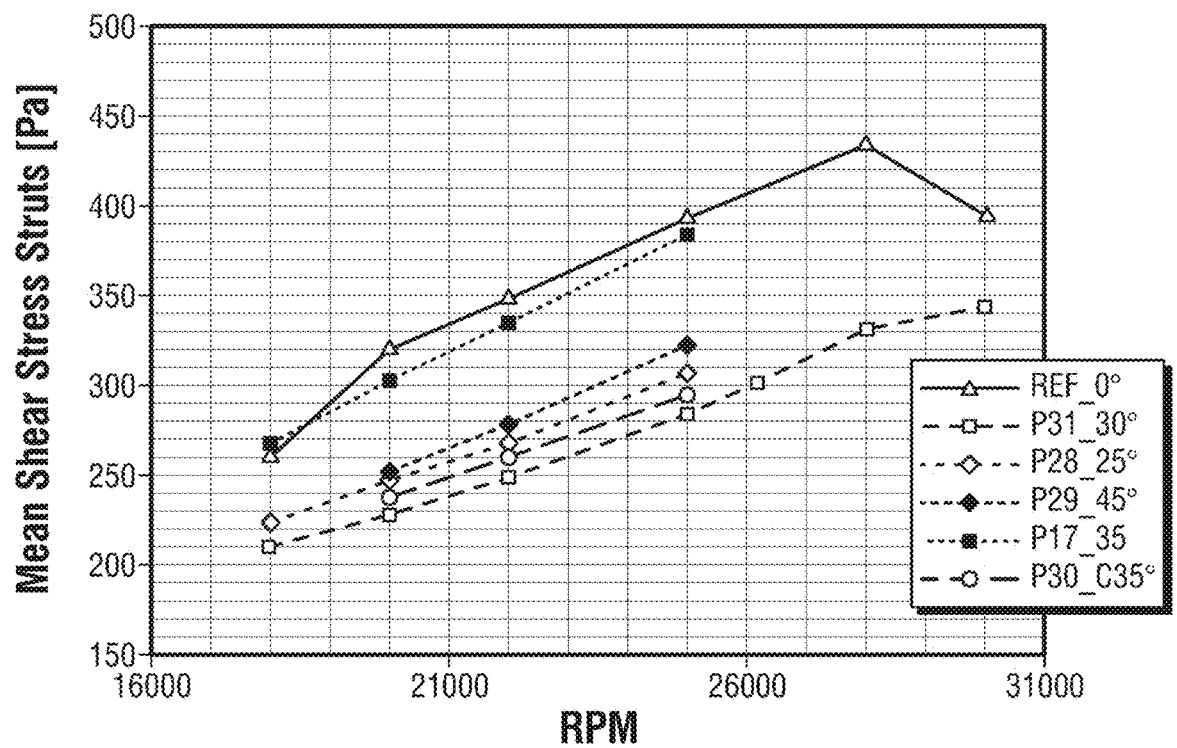
Figure 18A:
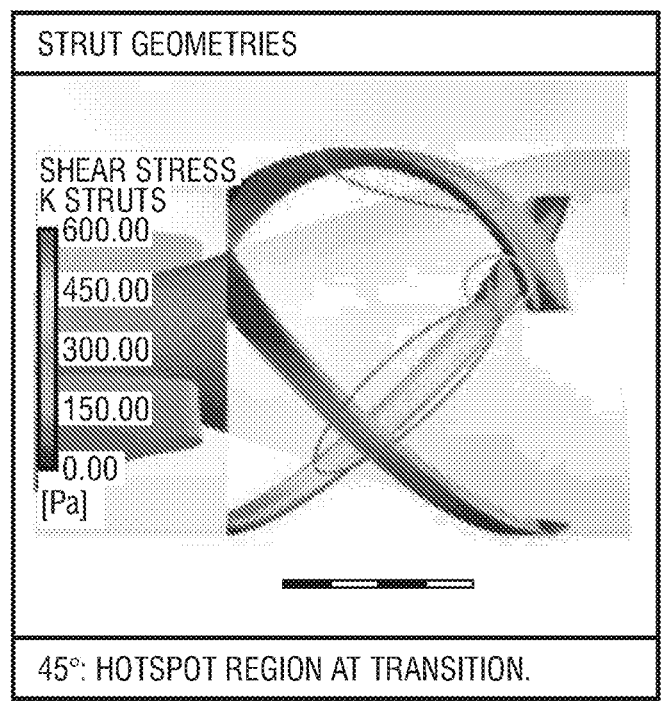
FIGS. 18a-18e clearly show how the overall mean shear along the pillars could be lowered.
Figure 18B:
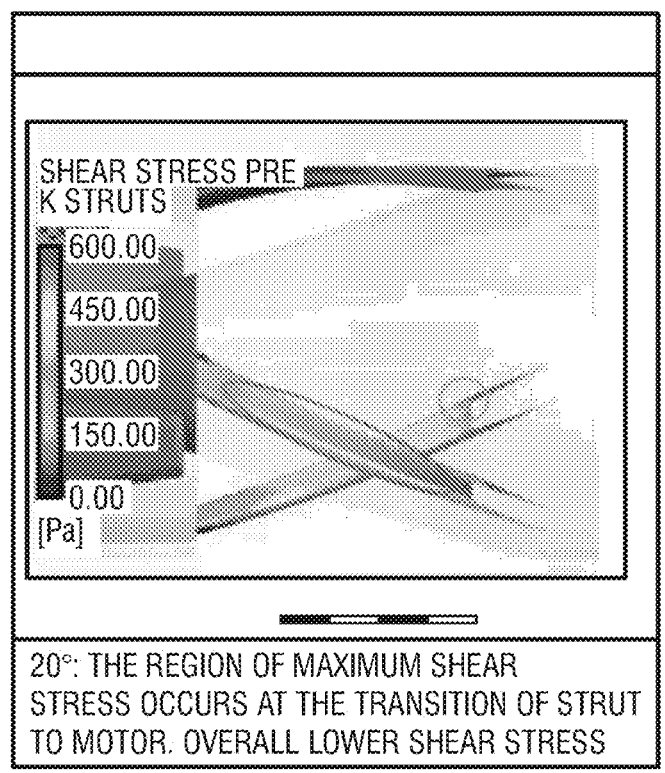
Figure 18C:
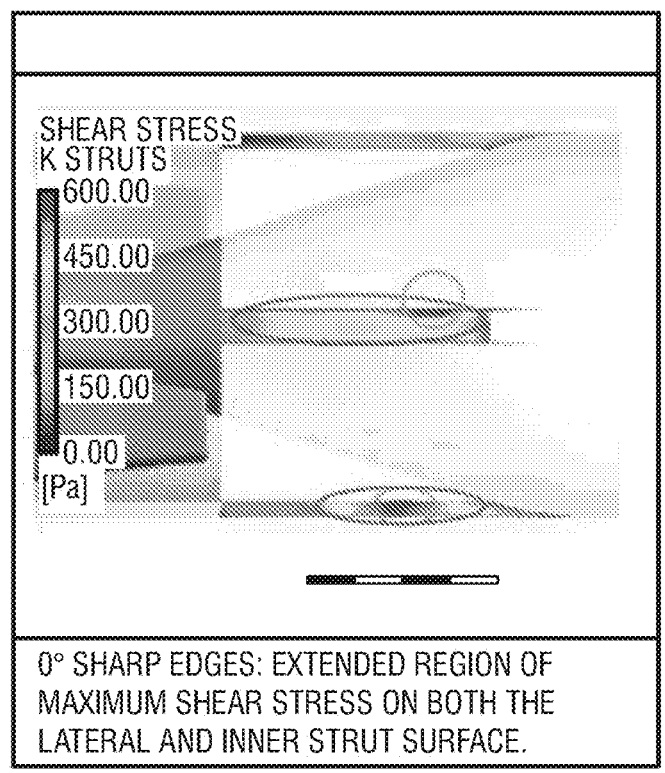
Figure 18D:
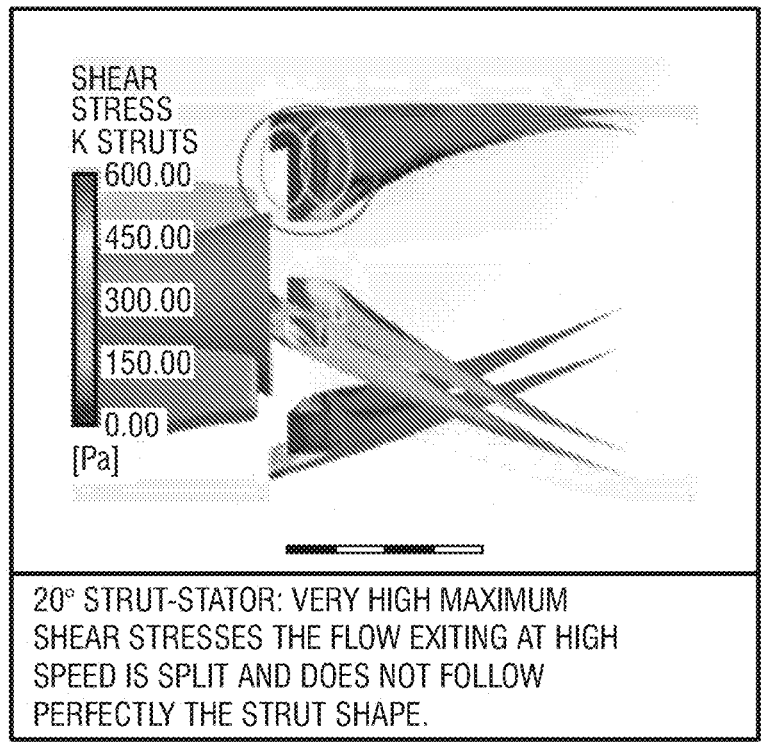
Figure 18E:
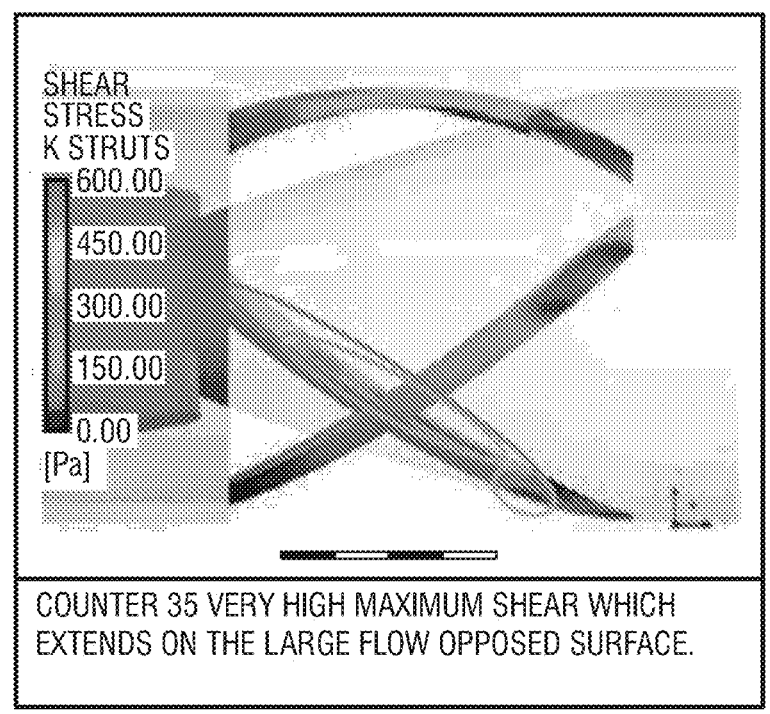

Pillars: FIGS. 17a-17b show the maximum and mean shear stress for the reference and P31 design. In the case of the pillar analysis the identification of the optimal geometry is not an obvious case. The orientation of the pillars causes higher maximum shear stresses. Comparing the oscillation between P_REF and P_31, it can be seen that through the alignment of the pillars less fluctuating events occurred. At the same time, the flow opposed surface is minimized and the overall mean shear stress could be significantly reduced. The following the trend for P_REF, the straight pillar design might be more beneficial for higher RPM ranges.

The following pictures depict the shear stress distribution at selected pillar geometries. The yellow circle indicates the region of maximum occurring shear while the blue circle covers the region of mean shear.

The charts and FIGS. 18a-18e clearly show how the overall mean shear along the pillars could be lowered. Best results seem to be feasible with the 30° angle orientation of the pillar geometry.

Impeller

Figure 19A:
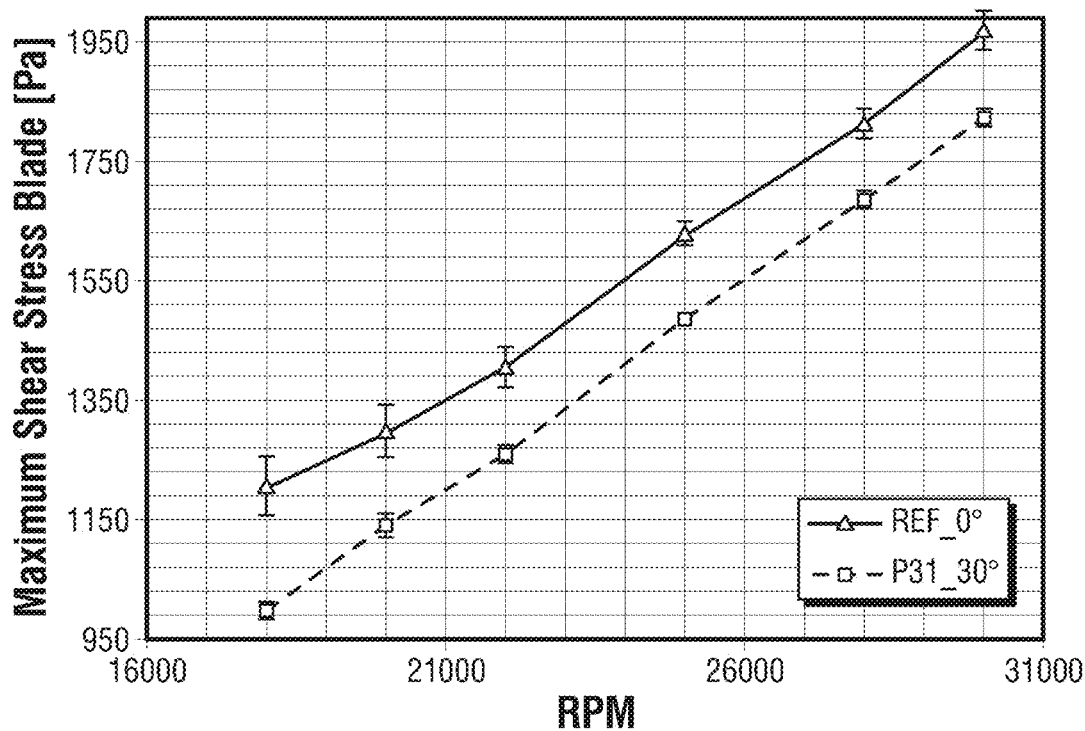
FIGS. 19a-19b show the maximum and mean shear stress for the reference and P31 design FIG. 20 show Lagrange hemolysis estimations with Heuser constants.
Figures 19B, 20:
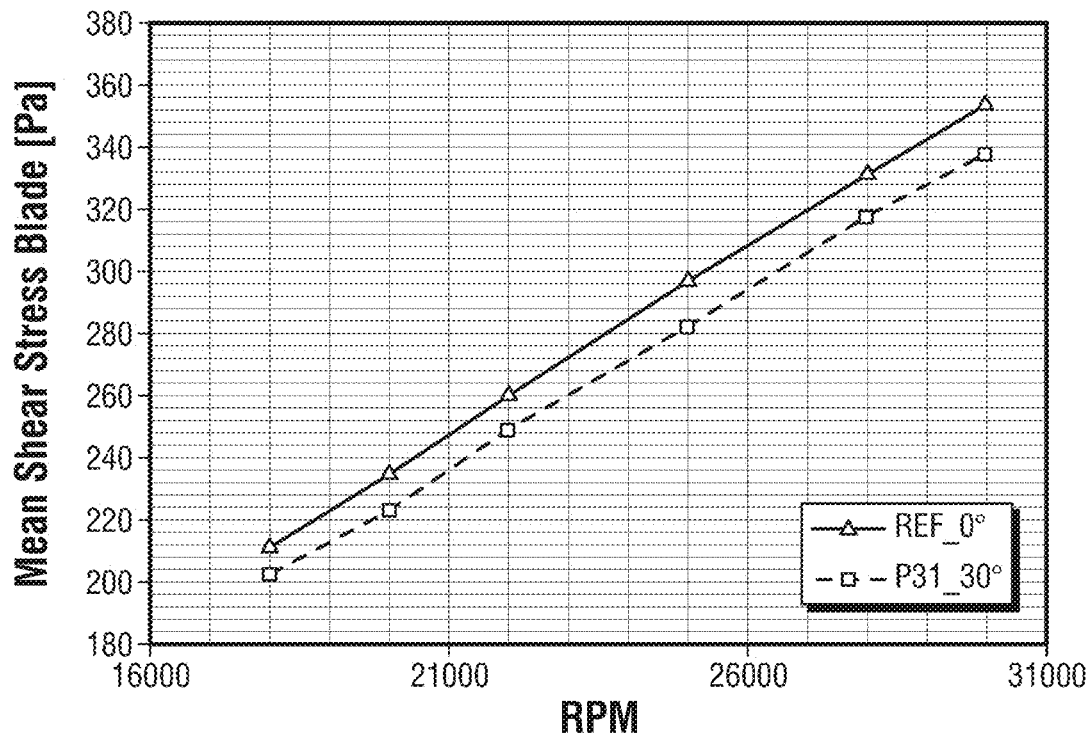

FIGS. 19a-19b show the maximum and mean shear stress for the reference and P31 design. The extension of the inlet shroud and multiple design iterations including a further extension of the hub (P_17, Milestone1), improved blade angle and wrap angle extent distribution, the inclination of the leading edge (P_22, P_26, P_31) as well as a refined rounding at the impeller leading edge from lead to a consistent offset in both maximum and mean shear stress distribution comparing P__31. The extension of shroud could furthermore reduce the impact of detached flow and turbulence on the impeller shear stress distribution and allowed for a refined optimization.

Hemolysis Estimation

The results indicate that high hemolysis is associated with high speed. While the experiments are not an actual representation of actual hemolysis, the experiments do detect significant changes in the geometry that lead to an overall lower shear stress distribution in the blood, and in this case, P_31 shows a lower overall hemolytic potential compared to P_Ref. The accumulation results have to be interpreted in a comparative manner. The absolute values should therefore be understood more qualitatively than quantitatively.

Figure 21:
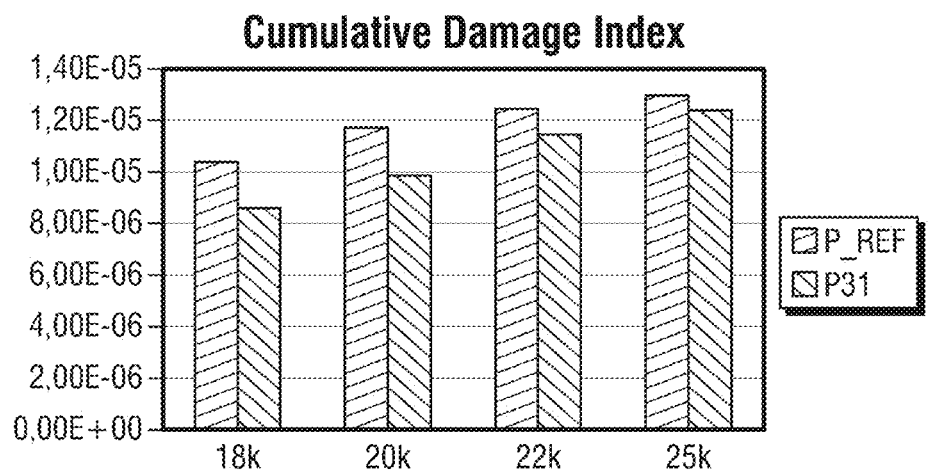
FIG. 21 shows the cumulative damage index for P_Ref and P_31.
Figure 22A:
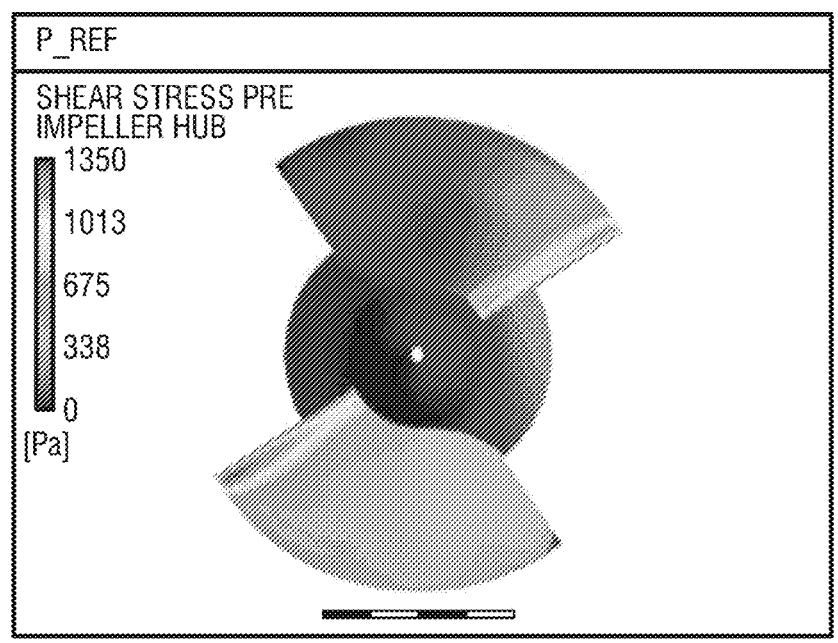
FIGS. 22a-22d illustrates the changes and improvements in shear reduction made to the impeller from P_ref to the new prototype P_31.
Figure 22B:
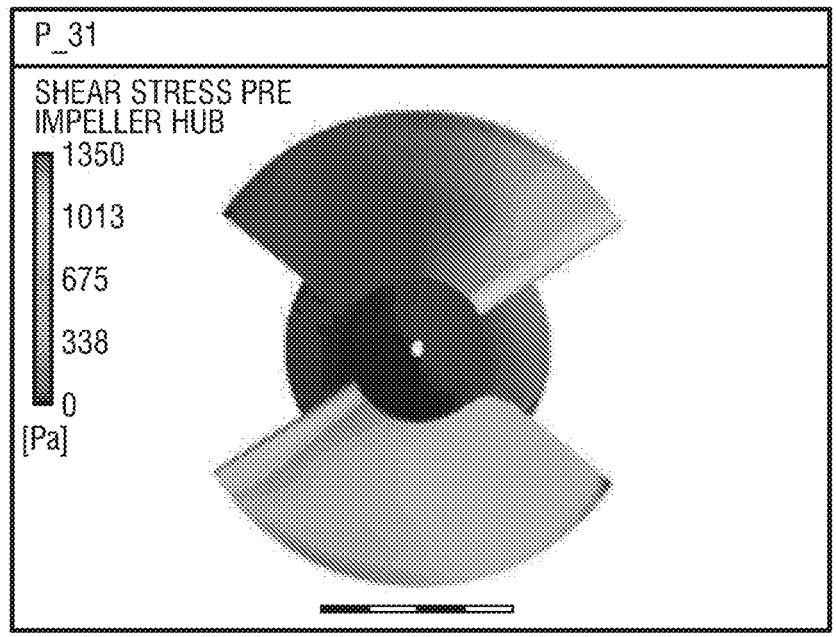
Figure 22C:
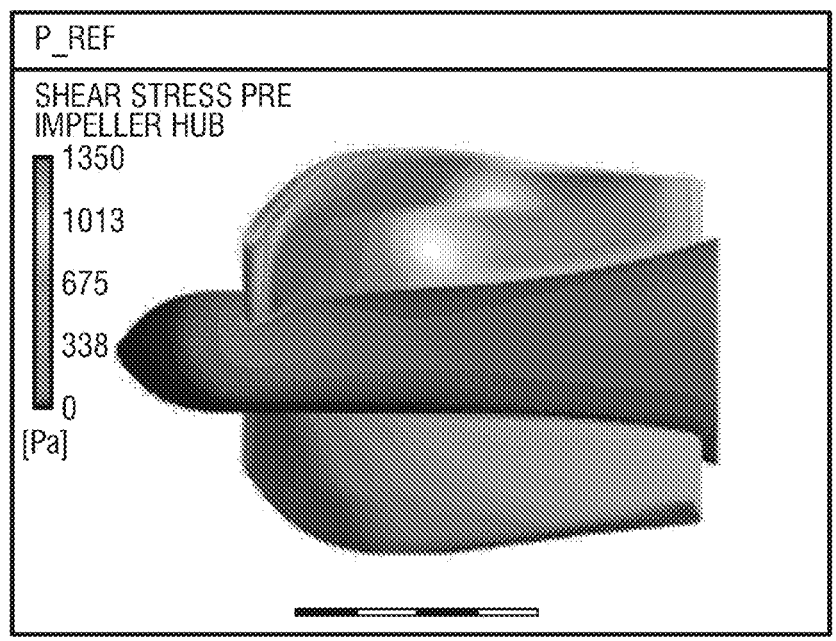
Figure 22D:
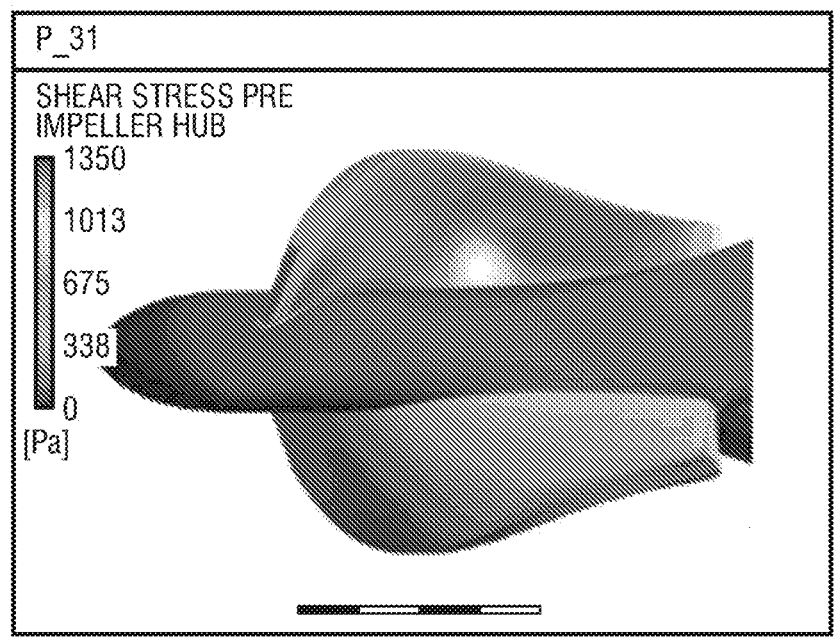

FIG. 20 show Lagrange hemolysis estimations with Heuser constants. FIG. 21 shows the cumulative damage index for P_Ref and P_31.

Discussion

FIGS. 22a-22d illustrates the changes and improvements in shear reduction made to the impeller from Pref to the new prototype P_31.

In milestone 1, various hemolysis hotspots were identified and the findings allowed the extension of the current to a more advanced evaluation setup. In milestone 2 of project phase III, 15 individual pump prototypes have been simulated and analyzed over a wide range of pump speeds.

The results of the optimization of the impeller show that a significant reduction of the maximum and mean shear stress for the investigated operational speed range of 18-25 k could be achieved. The combination of impeller P_31 with pillars that are oriented in a 30° angle combined with the proposed extension of inlet shroud proved to be the best combination among the investigated geometries. The overall pump hemolysis contribution has been investigated with a Lagrange particle approach and could furthermore identify a clear improvement. The presented prototype in the current configuration therefore gives raise for a promising perspective for future hemolysis tests.

Figure 23:
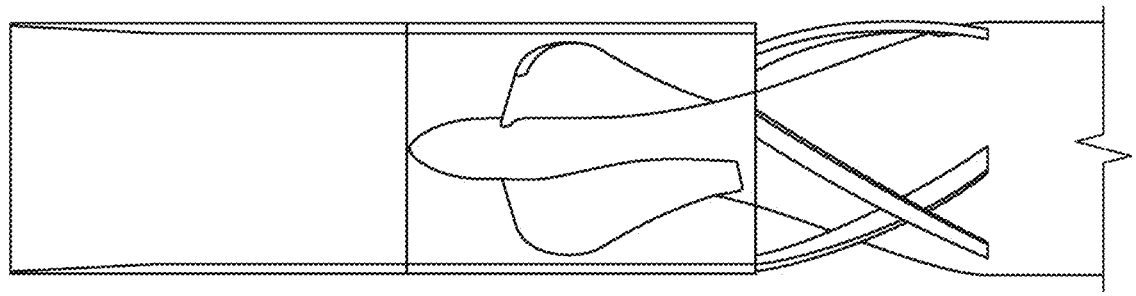
FIG. 23 shows a proposed prototype.

Overall, the results clearly show that additional improvements to the reference impeller were achieved. The new prototype P_31 features lower predicted hemolytic potential, increased efficiency and improved overall flow guidance. FIG. 23 shows a proposed prototype.

Figure 24:
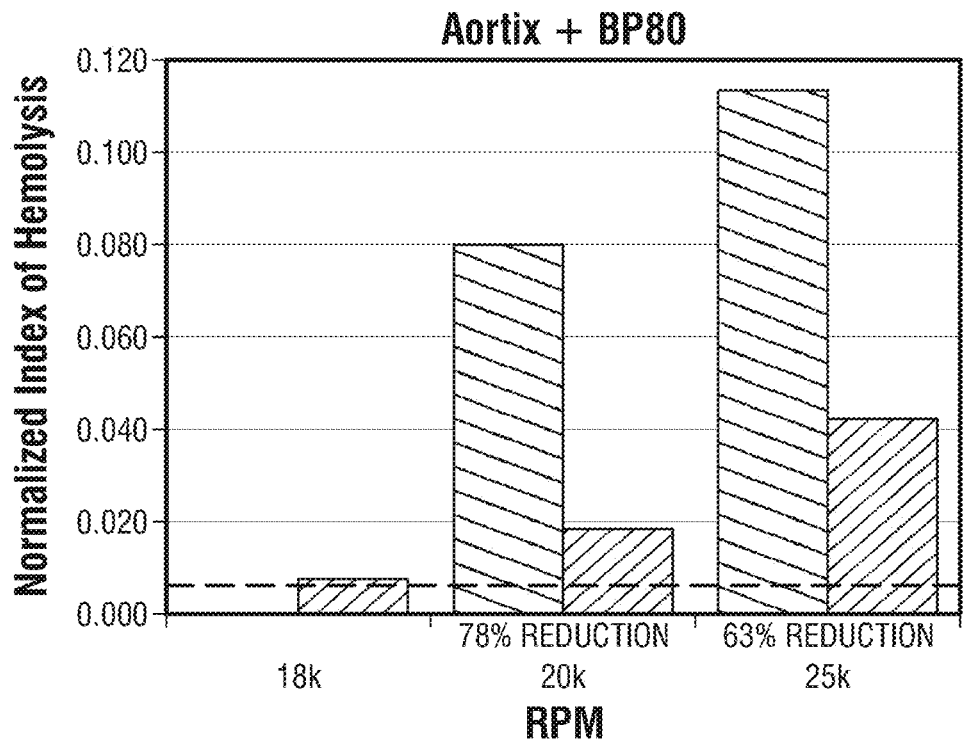
FIG. 24 shows the NIH at various rpm for prototypes.
Figure 25:
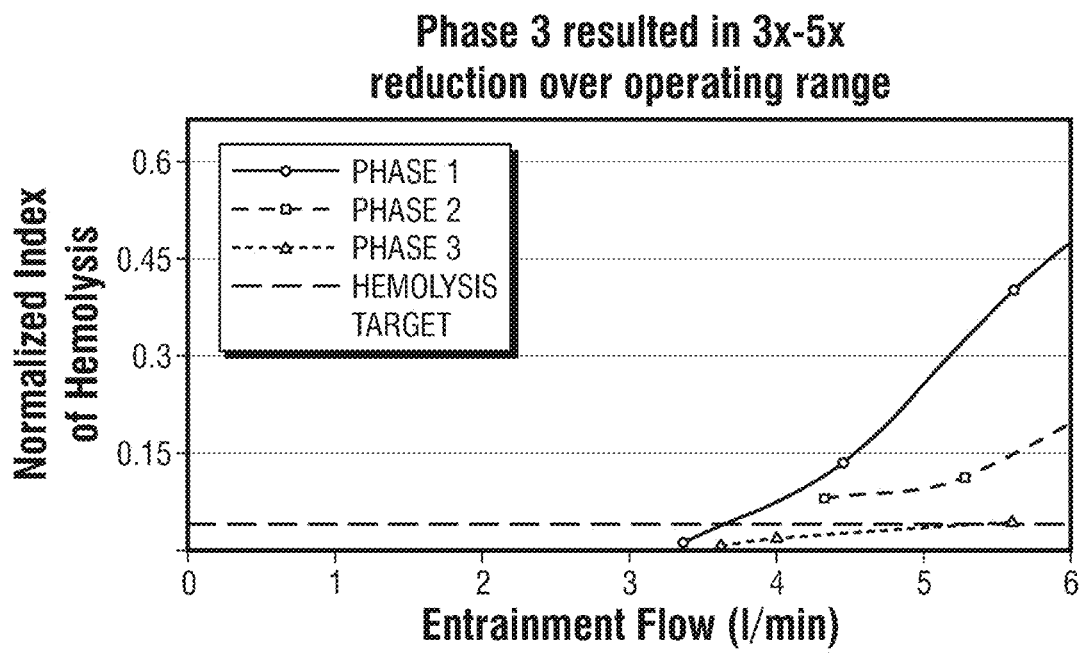
FIG. 25 shows the NIH v. entrainment flow for various phases of testing.

FIG. 24 shows the NIH at various rpm for prototypes. It can be seen from 20 k and 25 k that there are drastic reductions from the improved design. FIG. 25 shows the NIH v. entrainment flow for various phases of testing. It can be seen that that there is a drastic change in the NIH as designs progressed through various prototype phases.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

The invention claimed is:

1. A blood pump having a central axis and comprising:
    a shroud extending generally along the central axis, the shroud comprising an inlet for incoming blood flow and an outlet for outgoing blood flow;
    an impeller positioned within the shroud and extending generally along the central axis;
    a motor including a motor body disposed proximal to and coupled with the impeller, the motor extending generally along the central axis and configured to impart rotation to the impeller;
    a stator hub disposed adjacent to the motor body, the stator hub flaring radially outward in a proximal direction from a distal portion disposed at or within the shroud to a proximal portion spaced away from the shroud, the stator hub being stationary when rotation is imparted to the impeller by the motor; and
    a pillar having a first end coupled with a proximal portion of the shroud at the outlet of the shroud, the pillar extending to a second end opposite to the first end, the second end coupled to the motor body, a length of the pillar between the first end and the second end being unconnected to the stator hub, the pillar disposed non-parallel to the central axis.

2. The blood pump of claim 1, further comprising a plurality of pillars disposed about an outer periphery of the blood pump.

3. The blood pump of claim 2, wherein the impeller comprises a plurality of blades.

4. The blood pump of claim 1, further comprising a strut extending distally and radially outwardly of the inlet non-parallel to the central axis, the strut comprising an angled distal end portion.

5. The blood pump of claim 1, wherein a size of the inlet is larger than a size of the outlet.

6. A blood pump having a central axis and comprising:
a shroud extending generally along the central axis, the shroud comprising an inlet for incoming blood flow and an outlet for outgoing blood flow;
an impeller positioned within the shroud and extending generally along the central axis;
a motor body disposed proximal to and coupled with the impeller, the motor body extending generally along the central axis;
a stator hub adjacent the motor body and having a flared surface flaring radially outward in a proximal direction from a distal portion disposed at or within the shroud to a proximal portion spaced away from the shroud, the stator hub being stationary when rotation is imparted to the impeller by the motor body;
a pillar having a distal end coupled to a proximal end of the shroud and a proximal end coupled to the motor body, a length of the pillar spaced apart from the flared surface and disposed non-parallel to the central axis, the pillar and shroud comprising contiguous uninterrupted portions of a thin cylindrical shape.

7. The blood pump of claim 6, further comprising a plurality of pillars arranged peripherally around the blood pump.

8. The blood pump of claim 6, wherein the motor body comprises a motor to impart rotation to the impeller.

9. The blood pump of claim 6, further comprising a strut extending distally and radially outwardly of a distal portion of the shroud non-parallel to the central axis, the strut comprising an angled distal end portion.

10. The blood pump of claim 9, wherein the angled distal end portion comprises a bend at a distal-most end of the strut.

11. A blood pump having a central axis and comprising:
a shroud extending generally along the central axis, the shroud comprising an inlet for incoming blood flow and an outlet for outgoing blood flow;
an impeller positioned within the shroud;
a motor body disposed proximal to and coupled with the impeller;
a stator hub disposed adjacent the motor body and having a flared surface flaring radially outward in a proximal direction from a distal portion disposed at or within the shroud to a proximal portion spaced away from the shroud, the stator hub being stationary when rotation is imparted to the impeller by the motor body;
a pillar disposed outside of the shroud and extending from a proximal portion of the shroud to the motor body, the pillar disposed non-parallel to the central axis of the blood pump and supporting the shroud around the impeller.

12. The blood pump of claim 11, further comprising a strut extending distally and radially outwardly of the inlet of the shroud non-parallel to the central axis.

13. The intravascular blood pump of claim 12, wherein the strut comprises an angled distal end portion, and wherein the angled distal end portion comprises a bend at a distal-most end of the strut.

14. The intravascular blood pump of claim 11, further comprising a plurality of pillars extending across a space configured to convey blood out of the blood pump in operation.

15. The intravascular blood pump of claim 11, further comprising a plurality of pillars extending across a flow path of blood being pumped out of the blood pump in operation.

16. The intravascular blood pump of claim 15, wherein the flow path is bounded on one side by the flared surface of the stator hub.

17. The intravascular blood pump of claim 16, wherein the flared surface of the stator hub is disposed between a motor disposed in the motor body and the impeller.

* * * * *

UNITED STATES PATENT AND TRADEMARK OFFICE
CERTIFICATE OF CORRECTION

PATENT NO. : 12,078,192 B2
APPLICATION NO. : 17/588991
DATED : September 3, 2024
INVENTOR(S) : Sascha Gross-Hardt Page 1 of 1

It is certified that error appears in the above-identified patent and that said Letters Patent is hereby corrected as shown below:

In the Claims

In Column 14, Claim 13, Line 18 (approx.), delete "intravascular blood pump" and insert --blood pump--.

In Column 14, Claim 14, Line 22 (approx.), delete "intravascular blood pump" and insert --blood pump--.

In Column 14, Claim 15, Line 26 (approx.), delete "intravascular blood pump" and insert --blood pump--.

In Column 14, Claim 16, Line 29 (approx.), delete "intravascular blood pump" and insert --blood pump--.

In Column 14, Claim 17, Line 32 (approx.), delete "intravascular blood pump" and insert --blood pump--.

Signed and Sealed this
Twenty-fourth Day of June, 2025

Coke Morgan Stewart
*Acting Director of the United States Patent and Trademark Office*